US012735451B2

(12) United States Patent
Hokari et al.

(10) Patent No.: US 12,735,451 B2
(45) Date of Patent: Sep. 15, 2026

(54) PEPTIDE, CELL GROWTH PROMOTER, PROTEIN PRODUCTION PROMOTER, CULTURE MEDIUM, CELL GROWTH METHOD USING PEPTIDE, AND PROTEIN PRODUCTION METHOD USING PEPTIDE

(71) Applicant: Maruhachi Muramatsu, Inc., Shizuoka (JP)

(72) Inventors: Yoshinori Hokari, Shizuoka (JP); Natsuko Narawa, Shizuoka (JP); Keita Aoshima, Shizuoka (JP); Harumi Sugiya, Shizuoka (JP); Aya Sekine, Shizuoka (JP)

(73) Assignee: MARUHACHI MURAMATSU, INC., Shizuoka (JP)

( * ) Notice: Subject to any disclaimer, the term of this patent is extended or adjusted under 35 U.S.C. 154(b) by 470 days.

(21) Appl. No.: 18/267,509

(22) PCT Filed: Dec. 22, 2020

(86) PCT No.: PCT/JP2020/048023
§ 371 (c)(1),
(2) Date: Jun. 15, 2023

(87) PCT Pub. No.: WO2022/137357
PCT Pub. Date: Jun. 30, 2022

(65) Prior Publication Data

US 2024/0101599 A1 Mar. 28, 2024

(51) Int. Cl.
*C07K 5/083* (2006.01)
*C07K 5/093* (2006.01)

(52) U.S. Cl.
CPC .......... *C07K 5/0806* (2013.01); *C07K 5/0819* (2013.01)

(58) Field of Classification Search
None
See application file for complete search history.

(56) References Cited

U.S. PATENT DOCUMENTS

| | | | |
|---|---|---|---|
| 6,537,782 | B1 | 3/2003 | Shibuya et al. |
| 2004/0072341 | A1 | 4/2004 | Katinger et al. |
| 2009/0143248 | A1 | 6/2009 | Wilkins et al. |
| 2011/0183413 | A1 | 7/2011 | Wilkins et al. |
| 2011/0207174 | A1 | 8/2011 | Katayama et al. |
| 2017/0088813 | A1 | 3/2017 | Wilkins et al. |
| 2017/0321187 | A1 | 11/2017 | Wilkins et al. |
| 2021/0163880 | A1 | 6/2021 | Wilkins et al. |

FOREIGN PATENT DOCUMENTS

| | | | |
|---|---|---|---|
| JP | 2003-137807 | A | 5/2003 |
| JP | 2003-334068 | A | 11/2003 |
| JP | 2003-137807 | A5 | 7/2006 |
| JP | 2007051127 | A * | 3/2007 |
| JP | 2010-538089 | A | 12/2010 |
| JP | 2011-046637 | A | 3/2011 |
| JP | 2012-052264 | A | 3/2012 |
| WO | 99/63058 | A1 | 12/1999 |
| WO | 2009/033024 | A1 | 3/2009 |
| WO | 2010/050448 | A1 | 5/2010 |
| WO | 2018/085565 | A2 | 5/2018 |
| WO | 2018/085565 | A3 | 5/2018 |

OTHER PUBLICATIONS

Stedwell, Corey N et al. Screening for phosphorylated and nonphosphorylated peptides by infrared photodissociation spectroscopy. Analytical chemistry vol. 84,22 (2012): 9907-12. doi:10.1021/ac3023058 (Year: 2012).*
Office Action issued Jan. 16, 2026 in Korean patent application No. 10-2023-7022069, with English machine translation thereof.
Stedwell, C.N. et al., "Screening for phosphorylated and nonphosphorylated peptides by infrared photodissociation spectroscopy", Analytical Chemistry, 2012, vol. 84, pp. 9907-9912; ISR.
Muraoka, M. et al., "Studies on separation of amino acids and related compounds. IV. Separation of diastereomeric tripeptides containing basic and acidic amino acid residue", Bulletin of the Chemical Society of Japan, 1968, vol. 41, No. 9, pp. 2134-2140; ISR.
International Search Report issued in PCT/JP2020/048023, dated Mar. 16, 2021, and English translation thereof.
International Preliminary Report on Patentablity dated Jun. 13, 2023 including Written Opinion dated Mar. 16, 2021, issued in PCT/JP2020/048023, and English translation thereof.
Chan et al., "Positional Preferences of Ionizable Residues in Gly-X-Y Triplets of the Collagen Triple-helix," *J. Biol Chem.*, 1997, vol. 272, No. 50, pp. 31441-31446.
Muraoka et al., "Studies on Separation of Amino Acids and Related Compounds. IV. Separation of Diastereomeric Tripeptides Containing Basic and Acidic Amino Acid Residue," *Bulletin of the Chemical Society*, 1986, vol. 41, No. 9, pp. 2134-2140.
Persikov et al., "Peptide Investigations of Pairwise Interactions in the Collagen Triple-helix," *J. Mol. Biol.*, 2002, vol. 316, pp. 385-394.

(Continued)

*Primary Examiner* — Sudhakar Katakam
*Assistant Examiner* — Zachary J Miknis
(74) *Attorney, Agent, or Firm* — Greenblum & Bernstein, P.L.C.

(57) ABSTRACT

An object is to provide a synthetic culture medium not containing animal-derived components. In particular, an object is to provide a culture medium not containing animal-derived components but containing peptides that promote cell growth or contribute to promotion of protein production. A culture medium containing a peptide selected from the group consisting of Gly-Glu-Lys (GEK), Asp-Gly-Pro (DGP), Ala-Gly-Lys (AGK), Gly-Pro-Pro (GPP), Gly-Gly-Pro (GGP), Ala-Glu-Lys (AEK), Ala-Gly-Gly (AGG), Ala-Ser-Asn (ASN), and Glu-Gly-Lys (EGK) is provided.

1 Claim, 28 Drawing Sheets

(56) References Cited

OTHER PUBLICATIONS

Bhattacharjee et al., "Degradation of fibrin-β amyloid co-aggregate: A novel function attributed to ubiquitin," *BBA-Molecular Cell Research*, 2018, vol. 1865, pp. 1465-1478.
Office Action dated Sep. 24, 2024 issued in Japanese patent application No. 2023-178978, with English translation thereof.
Office Action dated Sep. 24, 2024 issued in Japanese patent application No. 2023-178979, with English translation thereof.
Office Action issued Oct. 7, 2024 in Singapore patent application No. 11202304758Q.
Office Action issued Oct. 29, 2024 in Japanese patent application No. 2022-166686, with English translation thereof.
Office Action issued Jul. 19, 2022 in Japanese patent application No. 2022-523975.
Office Action issued May 21, 2024 in Japanese patent application No. 2022-166686.
Jaliashvili, T.A., "Influence of oligopeptides on activity of adenylate cyclases and phosphodiesterases in fractions enriched in glia cells and synaptosome," *Investiya Akademii Nauk Gruzinskoi SSR, Seriya Biologicheskaya*, vol. 7, No. 4, 1981, pp. 357-362 (in Russian, with English translation).
Chi et al., "Isolation and characterization of three antioxidant peptides from protein hydrolysate of bluefin leather jacket (*Navodon septentrionalis*) heads," *Journal of Functional Foods*, 2015, vol. 12, pp. 1-10.
Office Action issued Aug. 1, 2025 in Singapore Patent Application No. 11202304758Q.
Office Action dated Jun. 15, 2026, issued in Singapore patent application No. 11202304758Q.

* cited by examiner

Peptide Time Kinetics

AMOUNT OF PROTEIN PRODUCED
AMOUNT OF PROTEIN PRODUCED (mg/L)
90.00
80.00
70.00
60.00
50.00
40.00
30.00
20.00
10.00
0.00
3
4
5
6
7
NUMBER OF DAYS OF CELL CULTURE (DAY)
BASAL MEDIUM
MEDIUM SUPPLEMENTED WITH VITAMINS AND LIKE
AGK 3.95mM
GPP 4.40mM

PEPTIDE, CELL GROWTH PROMOTER, PROTEIN PRODUCTION PROMOTER, CULTURE MEDIUM, CELL GROWTH METHOD USING PEPTIDE, AND PROTEIN PRODUCTION METHOD USING PEPTIDE

TECHNICAL FIELD

The present invention relates to a peptide. The present invention particularly relates to a novel tripeptide suitable for animal cell culture, a cell growth promoter containing the peptide, a protein production promoter, a culture medium, a cell growth method using the peptide, and a protein production method using the peptide.

BACKGROUND ART

For the purpose of animal cell growth, mammal-derived extracts such as fetal bovine serum and fish meat-related components are added in addition to nutrient components such as vitamins, amino acids, salts, and saccharides when trying to obtain a natural protein produced by animal cells by culturing animal cells or when producing a desired protein and the like by culturing animal cells into which a gene encoding the desired protein has been introduced (PTL 1 and PTL 2).

However, the mammal-derived extracts such as fetal bovine serum are added at about 5% to 20% with respect to a culture medium, and there was a problem in that they account for 75% to 95% of the cost of the culture medium, and that there were lot differences in quality because they were derived from animals. Furthermore, because there is concern about the correlation with mad cow disease, bovine spongiform encephalopathy, transmissible spongiform encephalopathy, Creutzfeldt-Jakob disease, and the like, culture media not containing the mammal-derived extracts such as fetal bovine serum have also been tried, but this resulted in another problem in which there was a significant decrease in cell viability at the early stage of culture, and it was difficult to perform long-term culture and large-scale culture.

Furthermore, the problems of cost and decrease in cell viability at the early stage of culture were solved by adding fish meat extracts, and fish meat-related components, which are enzyme decomposition products of fish meat. However, there remains a problem in that there are lot differences in quality associated with animal origin. Furthermore, because the component details of the fish meat-related components are unclear and the components vary depending on the type and the part of target fish and the conditions for enzyme decomposition, there is a problem in that there are various unknown risks when used as a culture medium, making safe use difficult.

CITATION LIST

Patent Literature

[PTL 1] WO 99/63058

[PTL 2] Japanese Patent Application Publication No. 2003-334068

SUMMARY OF INVENTION

Technical Problem

An object of the present invention is to provide a synthetic culture medium not containing animal-derived components.

In particular, an object is to provide a culture medium not containing animal-derived components but containing peptides that promote cell growth or contribute to promotion of protein production.

Solution to Problem

As a result of intensive studies in view of the above-mentioned circumstances, the inventors of the present invention found a peptide that promotes cell growth and contributes to the promotion of protein production, and found a cell growth promoter containing the peptide, a protein production promoter containing the peptide, and a culture medium containing the peptide.

In other words, a peptide of the present invention is characterized by being selected from the group consisting of Gly-Glu-Lys (GEK), Asp-Gly-Pro (DGP), Ala-Gly-Lys (AGK), Gly-Pro-Pro (GPP), Gly-Gly-Pro (GGP), Ala-Glu-Lys (AEK), Ala-Gly-Gly (AGG), Ala-Ser-Asn (ASN), and Glu-Gly-Lys (EGK).

A cell growth promoter of the present invention is characterized by containing one or more of the above-mentioned peptides.

A protein production promoter of the present invention is characterized by containing one or more of the above-mentioned peptides.

A culture medium of the present invention is characterized by containing the above-mentioned cell growth promoter or the above-mentioned protein production promoter.

A cell growth method of the present invention is characterized by using one or more of the above-mentioned peptides.

A protein production method of the present invention is characterized by using one or more of the above-mentioned peptides.

Advantageous Effects of Invention

According to the peptide of the present invention, it is possible to provide a cell growth promoter, a protein production promoter, and a culture medium, which do not contain animal-derived components and into which chemically synthesized substances have been blended, and to provide a cell growth method and a protein production method. In other words, it is possible to provide a cell growth promoter, a protein production promoter, and a culture medium which have no concern about the correlation with mad cow disease and the like, have reduced cost, and have stable quality because the details of the components are clarified.

BRIEF DESCRIPTION OF DRAWINGS

FIG. 30 shows the viable cell count for each tripeptide in a cell growth test using a medium supplemented with vitamins and the like.

FIG. 31 shows the cell viability for each tripeptide in the cell growth test using the medium supplemented with vitamins and the like.

FIG. 32 shows the amount of protein produced by each tripeptide in a protein production test using a medium supplemented with vitamins and the like.

FIG. 33 shows the amount of protein produced by each tripeptide in the protein production test using the medium supplemented with vitamins and the like.

DESCRIPTION OF EMBODIMENTS

Figure 1:
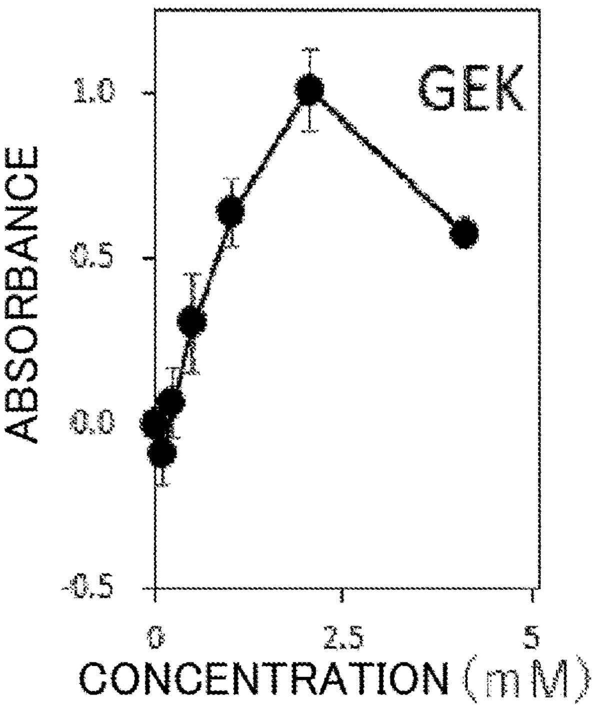
FIG. 1 shows the relationship between the concentration of GEK and the viable cell count (absorbance) in a cell growth test.
Figure 2:
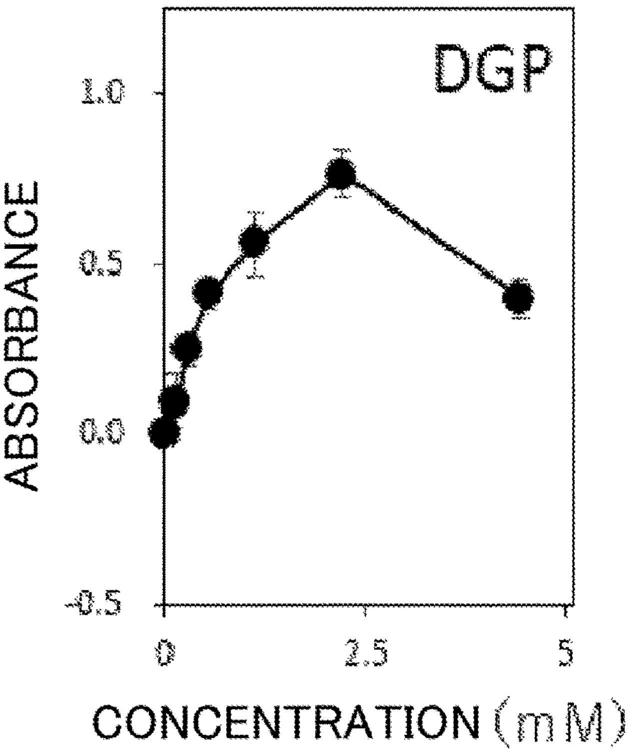
FIG. 2 shows the relationship between the concentration of DGP and the viable cell count (absorbance) in the cell growth test.
Figure 3:
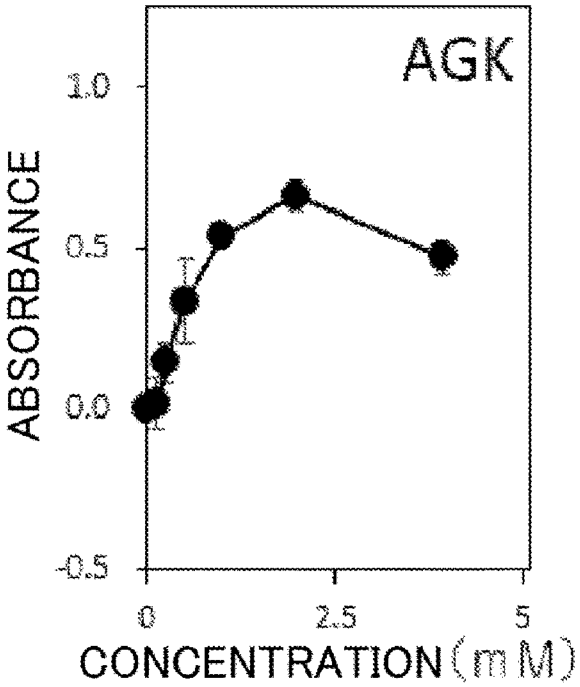
FIG. 3 shows the relationship between the concentration of AGK and the viable cell count (absorbance) in the cell growth test.
Figure 4:
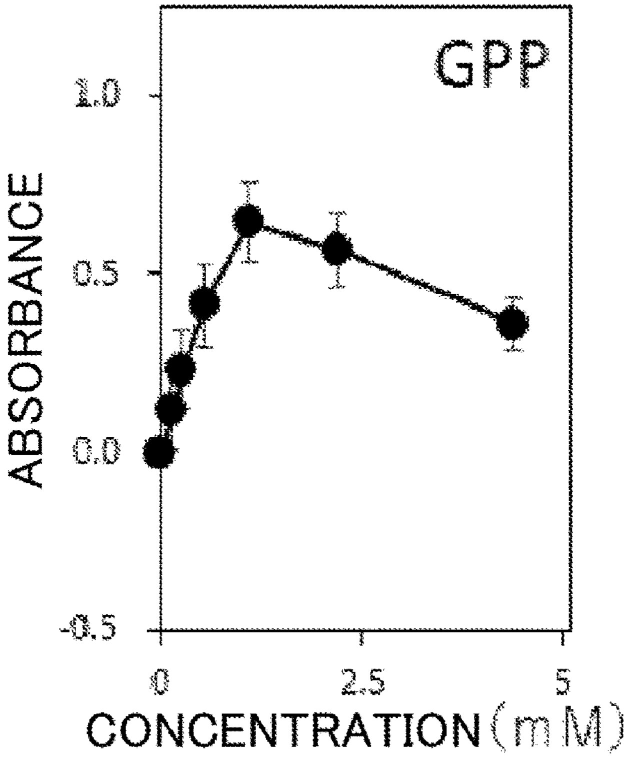
FIG. 4 shows the relationship between the concentration of GPP and the viable cell count (absorbance) in the cell growth test.
Figure 5:
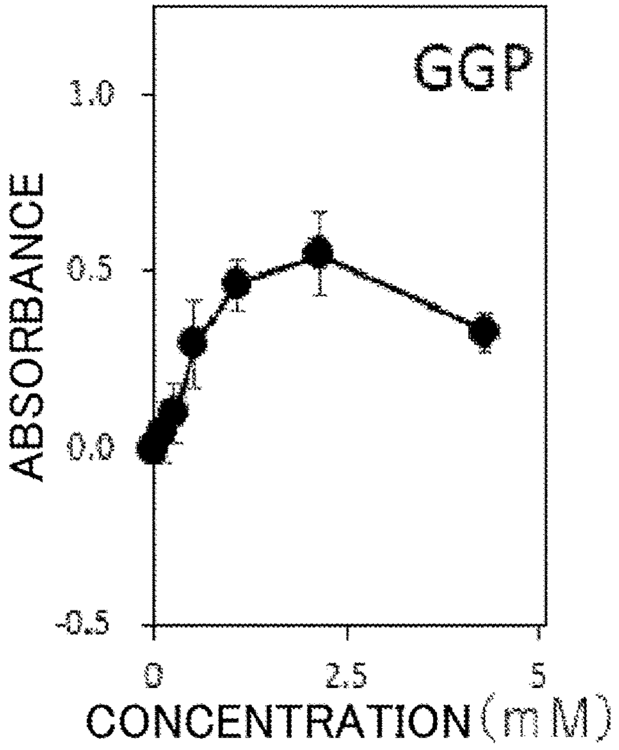
FIG. 5 shows the relationship between the concentration of GGP and the viable cell count (absorbance) in the cell growth test.
Figure 6:
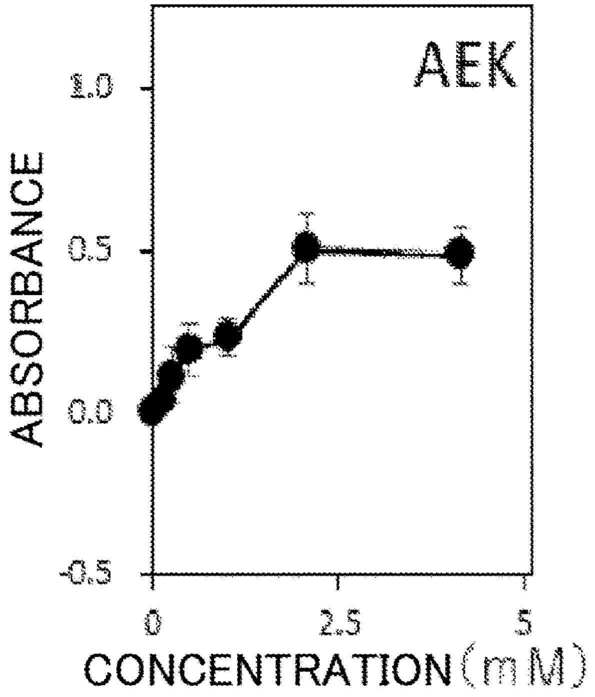
FIG. 6 shows the relationship between the concentration of AEK and the viable cell count (absorbance) in the cell growth test.
Figure 7:
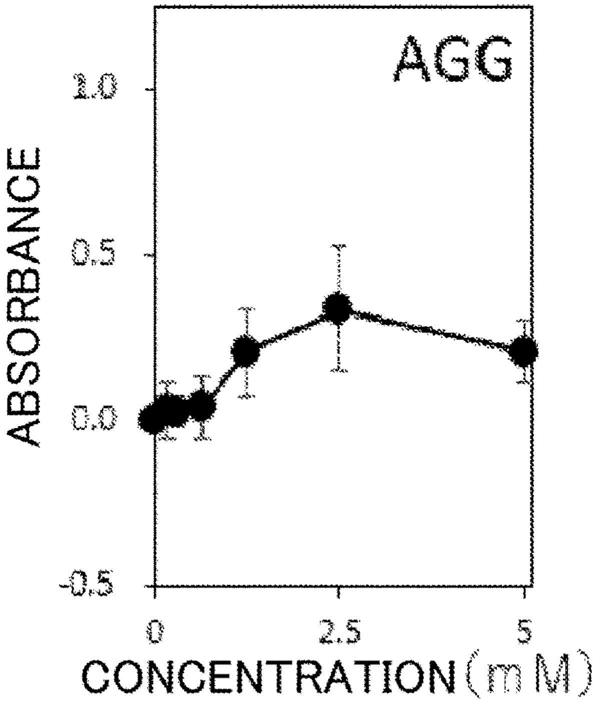
FIG. 7 shows the relationship between the concentration of AGG and the viable cell count (absorbance) in the cell growth test.
Figure 8:
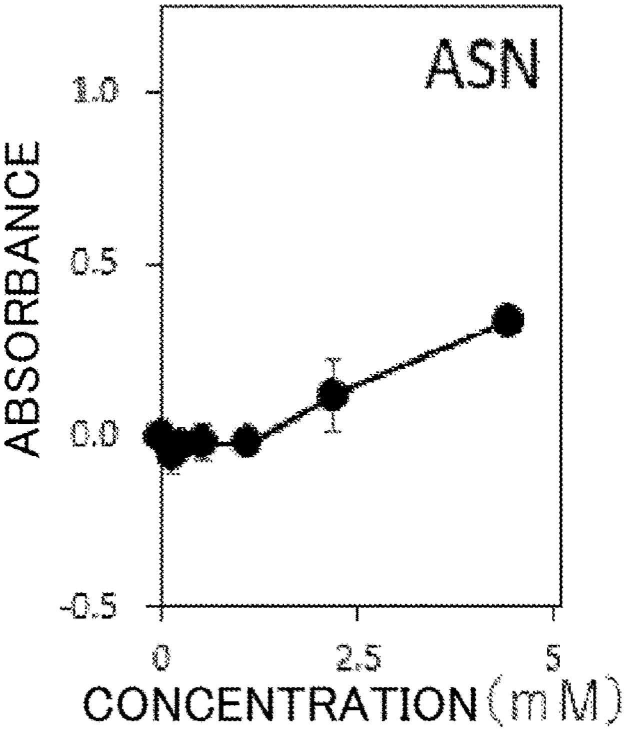
FIG. 8 shows the relationship between the concentration of ASN and the viable cell count (absorbance) in the cell growth test.
Figure 9:
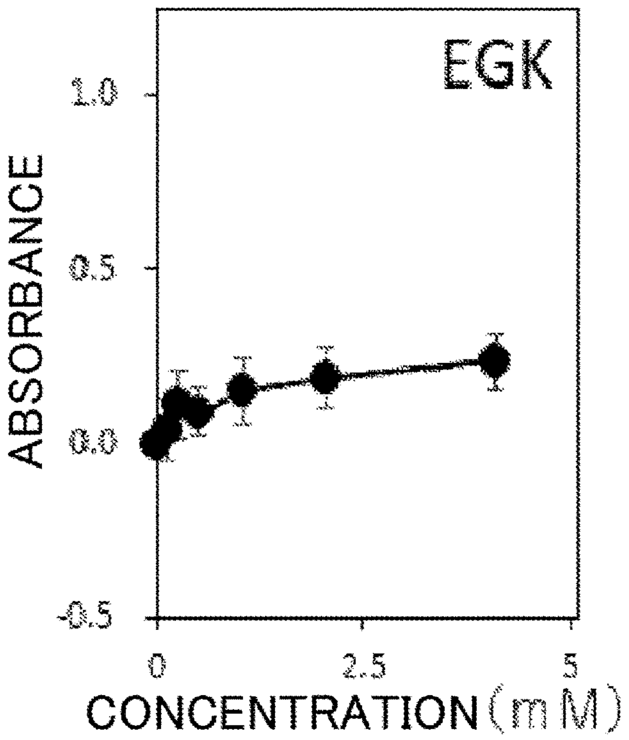
FIG. 9 shows the relationship between the concentration of EGK and the viable cell count (absorbance) in the cell growth test.
Figure 10:
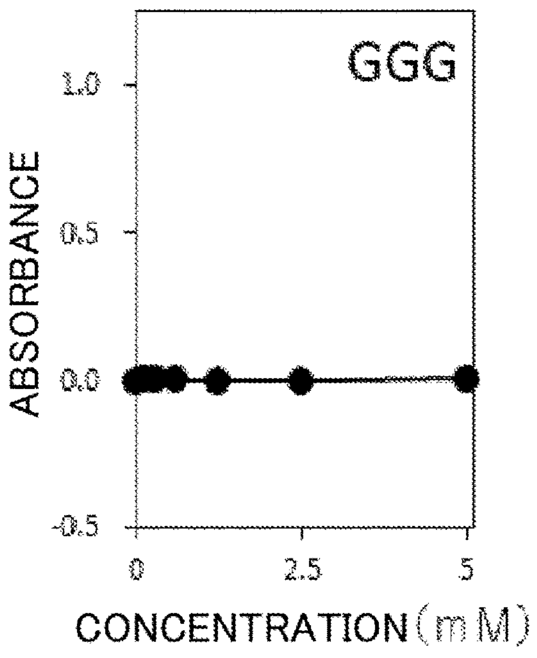
FIG. 10 shows the relationship between the concentration of GGG and the viable cell count (absorbance) in the cell growth test.

Embodiments of the present invention will be specifically described below.

(Peptide)

A peptide of the present invention is selected from the group consisting of Gly-Glu-Lys (GEK), Asp-Gly-Pro (DGP), Ala-Gly-Lys (AGK), Gly-Pro-Pro (GPP), Gly-Gly-Pro (GGP), Ala-Glu-Lys (AEK), Ala-Gly-Gly (AGG), Ala-Ser-Asn (ASN), and Glu-Gly-Lys (EGK). In addition, the above-mentioned peptide can be a pharmaceutically acceptable salt, and amino acids that do not change the activity of the peptide can be chemically modified. Among them, Gly-Glu-Lys (GEK), Asp-Gly-Pro (DGP), Ala-Gly-Lys (AGK), Gly-Pro-Pro (GPP), and Gly-Gly-Pro (GGP) are preferable.

The term "pharmaceutically acceptable salt" includes: inorganic acid salts such as hydrochlorides, phosphates, and sulfates; inorganic base salts such as sodium salts, potassium salts, and calcium salts; organic acid salts such as sulfonates, succinates, and oxalates; and organic base salts such as alkylammonium salts.

The phrase "amino acids that do not change the activity of the peptide can be chemically modified" means chemical modification of amino acids that do not significantly change the activity of the peptide even when the amino acids are chemically modified, and examples thereof include C-terminal modification with an amide, an ester, an acyl group, or the like, and N-terminal modification with an acetyl group.

The above-mentioned proline (Pro (P)) may be hydroxyproline (Hyp) into which a hydroxyl group is introduced.

The above-mentioned tripeptides were intensively searched for by fractionating hundreds of peptides with various lengths, which are mainly contained in fish meat extracts and their enzyme decomposition products, under various conditions to identify which of them promotes animal cell growth and which of them promotes protein production, and then confirming their effects for each peptide.

The above-mentioned peptide can be obtained by a method of fractionation from fish meat extracts and their enzyme decomposition products, by chemical synthesis methods including peptide synthesis methods, or by means such as expression by a recombinant DNA method.

In the method of fractionation from fish meat extracts and their enzyme decomposition products or the like, fractionation and isolation are carried out by adjusting various conditions of gel filtration chromatography and normal phase/reverse phase HPLC. In the chemical synthesis method, a peptide having a specific sequence can be obtained with synthesized amino acids or by synthesizing chemically modified amino acids by a chemical reaction. In the recombinant DNA method, a desired peptide can be obtained by generating recombinant proteins containing a plurality of peptide sequences from recombinant cells, purifying these proteins, and thereafter decomposing by enzymatic treatment or chemical treatment.

Cell Growth Promoter

A cell growth promoter of the present invention contains one or more of peptides selected from the group consisting of Gly-Glu-Lys (GEK), Asp-Gly-Pro (DGP), Ala-Gly-Lys (AGK), Gly-Pro-Pro (GPP), Gly-Gly-Pro (GGP), Ala-Glu-Lys (AEK), Ala-Gly-Gly (AGG), Ala-Ser-Asn (ASN), and Glu-Gly-Lys (EGK). In addition, the cell growth promoter of the present invention promotes cell growth as compared to the case in which the one or more peptides are not contained.

The above-mentioned peptide can be a pharmaceutically acceptable salt, and amino acids that do not change the activity of the peptide can be chemically modified. The above-mentioned proline (Pro (P)) may be hydroxyproline (Hyp) into which a hydroxyl group is introduced.

Peptides are selected by appropriately combining one or more of the above-mentioned peptides.

Among them, in the case of one type, Gly-Glu-Lys (GEK), Asp-Gly-Pro (DGP), Ala-Gly-Lys (AGK), Gly-Pro-Pro (GPP), and Gly-Gly-Pro (GGP) are more preferable.

In the case of two types, examples of preferable combinations include: Asp-Gly-Pro (DGP) and Ala-Gly-Lys (AGK); Gly-Glu-Lys (GEK) and Ala-Gly-Lys (AGK); Asp-Gly-Pro (DGP) and Gly-Glu-Lys (GEK); Gly-Pro-Pro (GPP) and Ala-Gly-Lys (AGK); and Gly-Pro-Pro (GPP) and Gly-Glu-Lys (GEK).

In the case of three types, examples of preferable combinations include: a combination of Gly-Pro-Pro (GPP)+Asp-Gly-Pro (DGP)+Gly-Glu-Lys (GEK), a combination of Gly-Pro-Pro (GPP)+Asp-Gly-Pro (DGP)+Ala-Gly-Lys (AGK), and a combination of Gly-Pro-Pro (GPP)+Gly-Glu-Lys (GEK)+Ala-Gly-Lys (AGK).

(Protein Production Promoter)

A protein production promoter of the present invention contains one or more of peptides selected from the group consisting of Gly-Glu-Lys (GEK), Asp-Gly-Pro (DGP), Ala-Gly-Lys (AGK), Gly-Pro-Pro (GPP), Gly-Gly-Pro (GGP), Ala-Glu-Lys (AEK), Ala-Gly-Gly (AGG), Ala-Ser-Asn (ASN), and Glu-Gly-Lys (EGK). In addition, the protein production promoter of the present invention promotes protein production as compared to the case in which the one or more peptides are not contained.

The above-mentioned peptide can be a pharmaceutically acceptable salt, and amino acids that do not change the activity of the peptide can be chemically modified. The above-mentioned proline (Pro (P)) may be hydroxyproline (Hyp) into which a hydroxyl group is introduced.

Peptides are selected by appropriately combining one or more of the above-mentioned peptides.

Among them, in the case of one type, examples of preferable peptides include Gly-Glu-Lys (GEK), Asp-Gly-Pro (DGP), Ala-Gly-Lys (AGK), Gly-Pro-Pro (GPP), and Gly-Gly-Pro (GGP).

In the case of two types, examples of preferable combinations include: Asp-Gly-Pro (DGP) and Ala-Gly-Lys (AGK); Gly-Glu-Lys (GEK) and Ala-Gly-Lys (AGK); Asp-Gly-Pro (DGP) and Gly-Glu-Lys (GEK); Gly-Pro-Pro (GPP) and Ala-Gly-Lys (AGK); and Gly-Pro-Pro (GPP) and Gly-Glu-Lys (GEK).

In the case of three types, examples of preferable combinations include: a combination of Gly-Pro-Pro (GPP)+Asp-Gly-Pro (DGP)+Gly-Glu-Lys (GEK), a combination of Gly-Pro-Pro (GPP)+Asp-Gly-Pro (DGP)+Ala-Gly-Lys (AGK), and a combination of Gly-Pro-Pro (GPP)+Gly-Glu-Lys (GEK)+Ala-Gly-Lys (AGK).

(Culture Medium)

A culture medium of the present invention contains the above-mentioned cell growth promoter containing the above-mentioned peptides, or the above-mentioned protein production promoter containing the above-mentioned peptides.

The concentration of the peptides in the culture medium is appropriately set according to cells and culture conditions. In other words, regarding the amount of the peptides in the culture medium, a concentration that can maintain the survival of cells is the lower limit concentration, a concentration that maximizes the amount of cell growth and the amount of protein produced as compared to culture media to which the cell growth promoter or the protein production promoter is not added is the preferable concentration, and a maximum concentration that is not harmful as the composition of the culture medium is the upper limit concentration. An example of the concentration per one peptide is 0.1 mM to 50 mM, preferably 0.2 mM to 10 mM, and more preferably 0.5 mM to 5 mM with respect to the culture medium.

The culture medium can be appropriately blended with other components used in animal cell culture medium. Examples thereof include vitamins, nucleic acids, amino acids, inorganic salts, sugars, polyamines, carbohydrates, proteins, fatty acids, lipids, pH adjusters, zinc, copper, and selenium.

Examples of the vitamins include choline chloride, niacinamide, D-pantothenic acid hemicalcium salt, folic acid, cyanocobalamin, pyridoxal hydrochloride, riboflavin, biotin, myo-inositol, ascorbic acid, thiamine hydrochloride, and vitamin B12.

Examples of the nucleic acids include xanthine, hypoxanthine, uridine, guanine hydrochloride, inosine, guanosine, cytidine, thymidine, and adenine.

Examples of the amino acids include glycine, L-alanine, L-arginine hydrochloride, L-asparagine monohydrate, L-aspartic acid, L-cysteine hydrochloride monohydrate, L-cystine dihydrochloride, L-glutamic acid, L-glutamine, L-histidine hydrochloride monohydrate, L-isoleucine, L-leucine, L-lysine hydrochloride, L-methionine, L-phenylalanine, L-proline, L-serine, L-threonine, L-tryptophan, L-tyrosine disodium salt, L-valine, and arginine.

Examples of the inorganic salts include calcium chloride, magnesium sulfate, potassium chloride, sodium hydrogen carbonate, sodium chloride, and sodium dihydrogen phosphate monohydrate.

Examples of other ingredients include D-glucose, α-lipoic acid, phenolsulfonphthalein (phenol red), sodium pyruvate, AlbuMax (registered trademark) II, human transferrin (holo), ammonium metavanadate, copper sulfate, manganese chloride, sodium selenate, ethanolamine, glutathione, methotrexate, and insulin. Furthermore, depending on the purpose, serum components such as fetal bovine serum may be contained, but are not contained when the intention is to exclude animal-derived components from the culture medium.

(Cell Growth Method and Protein Production Method)

A cell growth method and a protein production method of the present invention are performed by blending the peptide of the present invention in the above-mentioned culture medium to culture various animal cells.

The cell growth method and the protein production method are exemplified below, but are not limited thereto.

Animal cells are acclimated to serum-free flotation using a basal medium. One or more of peptides selected from the group consisting of Gly-Glu-Lys (GEK), Asp-Gly-Pro (DGP), Ala-Gly-Lys (AGK), Gly-Pro-Pro (GPP), Gly-Gly-Pro (GGP), Ala-Glu-Lys (AEK), Ala-Gly-Gly (AGG), Ala-Ser-Asn (ASN), and Glu-Gly-Lys (EGK) are added to the basal medium. At this time, vitamins, nucleic acids, sugars, polyamines, and amino acids, which are components with which the basal medium is supplemented, may be added.

Using a bioreactor, the animal cells acclimated to the basal medium are seeded in the basal medium to which the peptides have been added to perform cell growth and protein production.

EXAMPLES

Next, the present invention will be specifically described with reference to examples, but these examples are not intended to limit the present invention.

(Measurement of Relationship Between Concentration of Each Peptide Solution and Viable Cell Count)

Peptides having the sequences of Gly-Glu-Lys (GEK), Asp-Gly-Pro (DGP), Ala-Gly-Lys (AGK), Gly-Pro-Pro (GPP), Gly-Gly-Pro (GGP), Ala-Glu-Lys (AEK), Ala-Gly-Gly (AGG), Ala-Ser-Asn (ASN), and Glu-Gly-Lys (EGK), and Gly-Gly-Gly (GGG) are synthesized to prepare each of peptide solutions at 10-fold concentrations shown in Tables 1 to 10.

A cell suspension prepared such that CHO-K1 (RI KEN BioResource Research Center, cell number: RCB2330) was at $3\times10^4$ cells/mL was seeded in a 96-well plate at 100 μL/well and cultured in an incubator at 37° C. and 5% $CO_2$ for 24 hours. As a culture medium, an MEMα culture medium (Gibco) containing 10% FBS was used.

After removing the culture medium from each well and washing with the MEMα culture medium (100 μL), 90 μL of a new MEMα culture medium was dispensed into each well, and each peptide solution (10 μL) was added (total 100 μL/well) such that final concentrations were within a range of 0 mM to 5 mM as shown in Tables 1 to 10 to perform culture for 5 days. A similar culture test was performed using a system containing neither peptide nor FBS as a comparative sample. After culturing for 5 days, 10 μL/well of a viable cell count measurement reagent SF (Nacalai Tesque Inc.) was added, and a color reaction was carried out in an incubator at 37° C. and 5% $CO_2$ for 2 hours to measure an absorbance at 450 nm with a plate reader. A reference wavelength was 630 nm. It was confirmed that the absorbance at 450 nm correlated with the cell number.

The above preparation, culture, and measurement were performed with n=3, and Tables 1 to 10 and FIGS. 1 to 10 show the absorbance at the concentration of each peptide solution.

TABLE 1

| Test section GEK(mM) | Absorbance (450 nm) | Standard deviation SD |
|---|---|---|
| 0 | 0.0000 | 0.0000 |
| 0.128 | −0.0903 | 0.0933 |
| 0.257 | 0.0657 | 0.1054 |
| 0.512 | 0.3020 | 0.1473 |
| 1.02 | 0.6377 | 0.1016 |
| 2.05 | 1.0050 | 0.1205 |
| 4.10 | 0.5757 | 0.0055 |

n = 3, average value

TABLE 2

| Test section DGP(mM) | Absorbance (450 nm) | Standard deviation SD |
|---|---|---|
| 0 | 0.0000 | 0.0000 |
| 0.138 | 0.0957 | 0.0779 |
| 0.278 | 0.2464 | 0.0453 |
| 0.555 | 0.4127 | 0.0450 |
| 1.11 | 0.5617 | 0.0947 |
| 2.22 | 0.7657 | 0.0716 |
| 4.44 | 0.4004 | 0.0580 |

n = 3, average value

TABLE 3

| Test section AGK(mM) | Absorbance (450 nm) | Standard deviation SD |
|---|---|---|
| 0 | 0.0000 | 0.0000 |
| 0.123 | 0.0180 | 0.0823 |
| 0.247 | 0.1440 | 0.0613 |
| 0.494 | 0.3360 | 0.1299 |
| 0.99 | 0.5380 | 0.0297 |
| 1.97 | 0.6613 | 0.0490 |
| 3.95 | 0.4693 | 0.0550 |

n = 3, average value

TABLE 4

| Test section GPP(mM) | Absorbance (450 nm) | Standard deviation SD |
|---|---|---|
| 0 | 0.0000 | 0.0000 |
| 0.137 | 0.1163 | 0.1072 |
| 0.276 | 0.2303 | 0.1138 |
| 0.550 | 0.4117 | 0.1168 |
| 1.10 | 0.6443 | 0.1129 |
| 2.20 | 0.5700 | 0.1032 |
| 4.40 | 0.3620 | 0.0721 |

n = 3, average value

TABLE 5

| Test section GGP(mM) | Absorbance (450 nm) | Standard deviation SD |
|---|---|---|
| 0 | 0.0000 | 0.0000 |
| 0.135 | 0.0420 | 0.0851 |
| 0.270 | 0.0966 | 0.0863 |
| 0.539 | 0.2946 | 0.1217 |
| 1.08 | 0.4653 | 0.0707 |
| 2.16 | 0.5483 | 0.1205 |
| 4.31 | 0.3286 | 0.0545 |

n = 3, average value

TABLE 6

| Test section AEK(mM) | Absorbance (450 nm) | Standard deviation SD |
|---|---|---|
| 0 | 0.0000 | 0.0000 |
| 0.129 | 0.0350 | 0.0250 |
| 0.259 | 0.1143 | 0.0840 |
| 0.516 | 0.1927 | 0.0850 |
| 1.03 | 0.2337 | 0.0570 |
| 2.06 | 0.5013 | 0.1066 |
| 4.13 | 0.4857 | 0.0873 |

n = 3, average value

TABLE 7

| Test section AGG(mM) | Absorbance (450 nm) | Standard deviation SD |
|---|---|---|
| 0 | 0.0000 | 0.0000 |
| 0.156 | 0.0277 | 0.0831 |
| 0.313 | 0.0274 | 0.0458 |
| 0.625 | 0.0967 | 0.0975 |
| 1.25 | 0.2064 | 0.1312 |
| 2.5 | 0.3357 | 0.1854 |
| 5 | 0.2080 | 0.0951 |

n = 3, average value

TABLE 8

| Test section ASN(mM) | Absorbance (450 nm) | Standard deviation SD |
|---|---|---|
| 0 | 0.0000 | 0.0000 |
| 0.138 | −0.0527 | 0.0550 |
| 0.276 | −0.0250 | 0.0273 |
| 0.552 | −0.0214 | 0.0506 |
| 1.10 | −0.0224 | 0.0129 |
| 2.21 | 0.1170 | 0.1066 |
| 4.42 | 0.3320 | 0.0070 |

n = 3, average value

TABLE 9

| Test section EGK(mM) | Absorbance (450 nm) | Standard deviation SD |
|---|---|---|
| 0 | 0.0000 | 0.0000 |
| 0.128 | 0.0383 | 0.0922 |
| 0.257 | 0.1123 | 0.0985 |
| 0.512 | 0.0893 | 0.0710 |
| 1.02 | 0.1503 | 0.0951 |
| 2.05 | 0.1876 | 0.0861 |
| 4.10 | 0.2373 | 0.0824 |

n = 3, average value

TABLE 10

| Test section GGG(mM) | Absorbance (450 nm) | Standard deviation SD |
|---|---|---|
| 0 | 0.0000 | 0.0000 |
| 0.156 | 0.0067 | 0.0080 |
| 0.313 | 0.0037 | 0.0056 |
| 0.625 | 0.0027 | 0.0066 |
| 1.25 | −0.0013 | 0.0036 |
| 2.5 | 0.0013 | 0.0031 |
| 5 | 0.0083 | 0.0006 |

n = 3, average value

From Tables 1 to 10 and FIGS. 1 to 10, it was found that, in the tested peptides except GGG, the addition of the peptide solution increased the cell number as compared to the case of no addition. In addition, it was found that the concentration of the peptide solution at which the cell number increased the most differed depending on the type of peptide.

Figure 11:
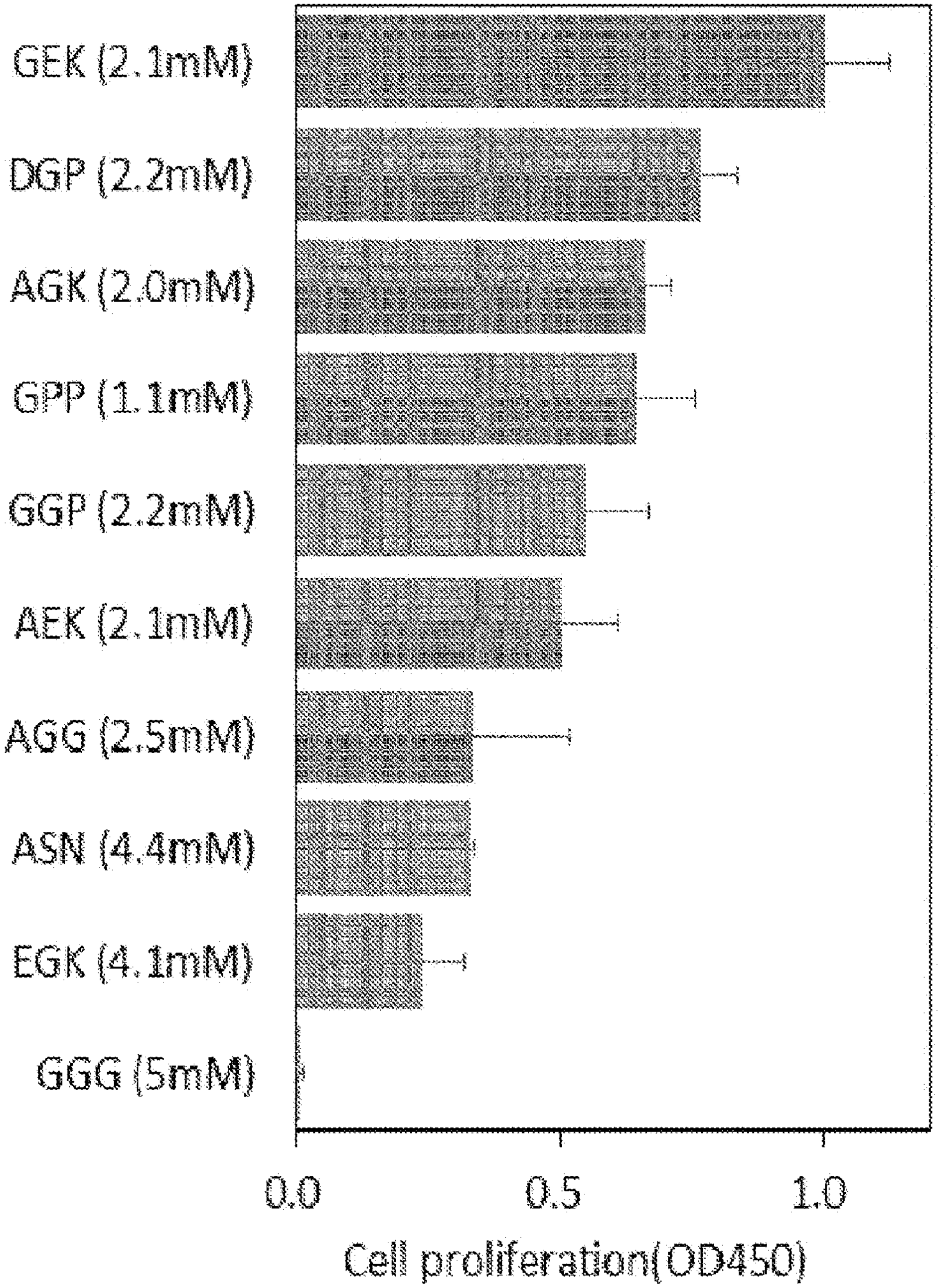
FIG. 11 shows the viable cell count (absorbance) for each tripeptide in the cell growth test.

Furthermore, the absorbance at the concentration of the peptide solution that increased the cell number the most is summarized in Table 11 and FIG. 11 for each peptide tested in order to compare and show the degree of cell growth promotion when the concentration of the peptide solution was optimized.

TABLE 11

| Peptides (concentration) | Concentration (mM) | Absorbance (450 nm) | Standard deviation SD |
|---|---|---|---|
| GGG (5 mM) | 5.0000 | 0.0083 | 0.0006 |
| EGK (4.1 mM) | 4.0997 | 0.2373 | 0.0824 |
| ASN (4.4 mM) | 4.4166 | 0.3320 | 0.0070 |
| AGG (2.5 mM) | 2.5000 | 0.3357 | 0.1854 |
| AEK (2.1 mM) | 2.0649 | 0.5013 | 0.1066 |
| GGP (2.2 mM) | 2.1566 | 0.5483 | 0.1205 |
| GPP (1.1 mM) | 1.1008 | 0.6443 | 0.1129 |
| AGK (2.0 mM) | 1.9745 | 0.6613 | 0.0490 |
| DGP (2.2 mM) | 2.2182 | 0.7657 | 0.0716 |
| GEK (2.1 mM) | 2.0488 | 1.0050 | 0.1205 |

It was found that, under the above-mentioned testing conditions, cell growth was promoted in the order of Gly-Glu-Lys (GEK), Asp-Gly-Pro (DGP), Ala-Gly-Lys (AGK), Gly-Pro-Pro (GPP), Gly-Gly-Pro (GGP), Ala-Glu-Lys (AEK), Ala-Gly-Gly (AGG), Ala-Ser-Asn (ASN), and Glu-Gly-Lys (EGK) as the sequences of the peptides.

(Measurement of Relationship Between Number of Days of Cell Growth of Each Peptide and Cell Number)

Peptides having the sequences of Gly-Pro-Pro (GPP), Asp-Gly-Pro (DGP), Gly-Glu-Lys (GEK), and Ala-Gly-Lys (AGK) were synthesized to prepare each peptide solution such that the concentration was a concentration at which the cell number increased the most within a range of 0 mM to 5 mM. In other words, Gly-Pro-Pro (GPP) was adjusted to 11 mM, Asp-Gly-Pro (DGP) was adjusted to 22 mM, Gly-Glu-Lys (GEK) was adjusted to 21 mM, and Ala-Gly-Lys (AGK) was adjusted to 20 mM, and an amount of 1/10 of the total culture medium volume was added to each well immediately before the cell culture test such that final concentrations were 1.1 mM, 2.2 mM, 2.1 mM, and 2.0 mM, respectively.

A cell suspension prepared such that CHO-K1 (RIKEN BioResource Research Center, cell number: RCB2330) was at $3\times10^4$ cells/mL was seeded in a 96-well plate at 100 μL/well and cultured in an incubator at 37° C. and 5% $CO_2$ for 24 hours. As a culture medium, an MEMα culture medium (Gibco) containing 10% FBS was used.

After removing the culture medium from each well and washing with the MEMα culture medium (100 μL), 90 μL of a new MEMα culture medium was dispensed into each well, and each peptide solution (10 μL) was added (total 100 μL/well) to perform culture for 0 to 5 days. Every day, 10 μL/well of a viable cell count measurement reagent SF (Nacalai Tesque Inc.) was added, and a color reaction was carried out in an incubator at 37° C. and 5% $CO_2$ for 2 hours to measure an absorbance at 450 nm with a plate reader. A reference wavelength was 630 nm. It was confirmed that the absorbance at 450 nm correlated with the cell number. A similar culture test was performed using a system containing neither peptide nor FBS as a comparative sample.

Figure 12:
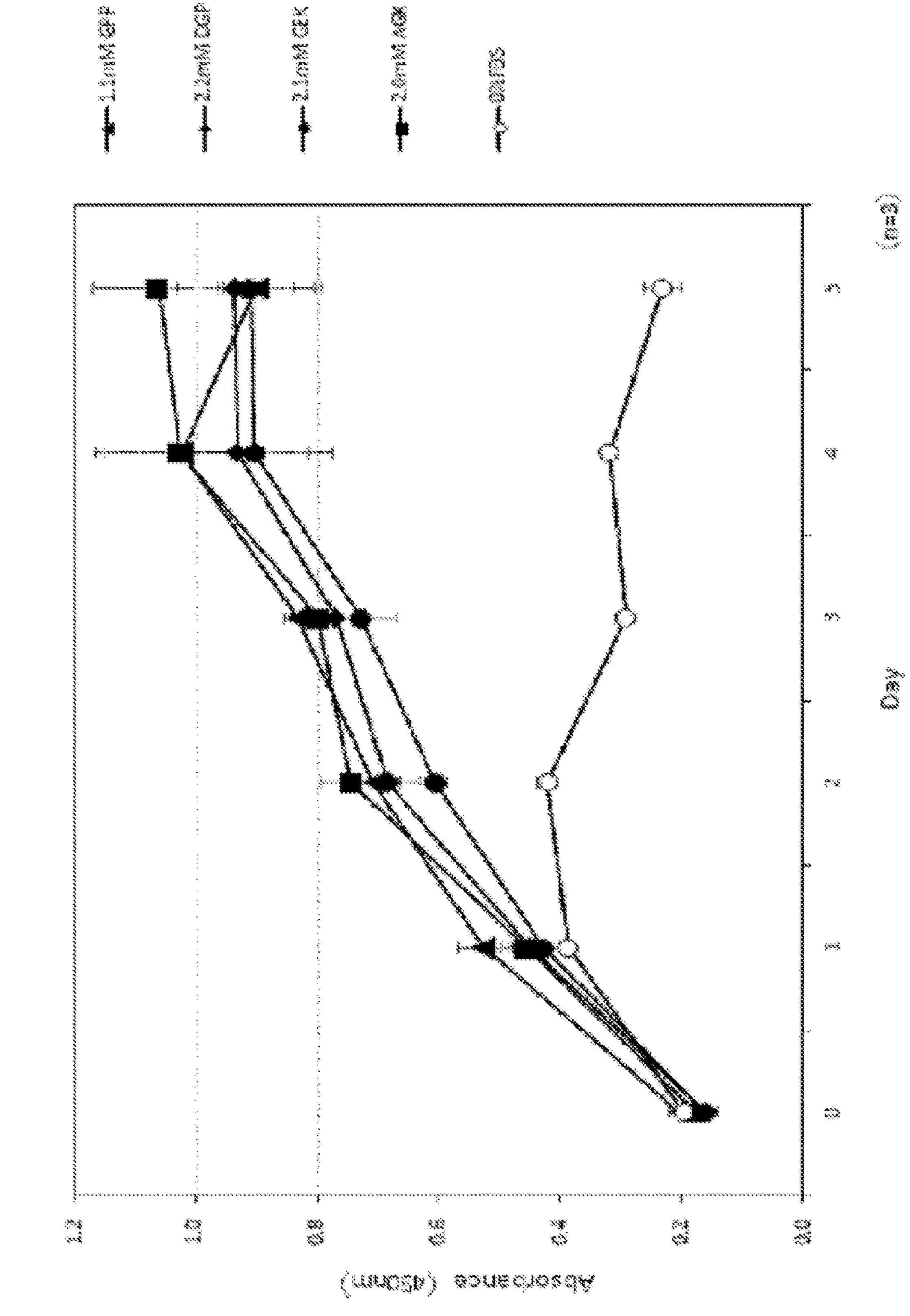
FIG. 12 shows time-dependent changes in the viable cell count (absorbance) for each tripeptide in the cell growth test.

The above preparation, culture, and measurement were performed with n=3, and Table 12 and FIG. 12 show the absorbance and the standard deviation of each peptide solution for each day.

TABLE 12

| | Day | | | | | |
|---|---|---|---|---|---|---|
| | 0 | 1 | 2 | 3 | 4 | 5 |
| OD450 (average value n = 3) | | | | | | |
| 1.1 mM GPP | 0.2023 | 0.5267 | 0.7083 | 0.8350 | 1.0227 | 0.9003 |
| 2.2 mM DGP | 0.1607 | 0.4507 | 0.6840 | 0.7700 | 0.9313 | 0.9363 |
| 2.1 mM GEK | 0.1613 | 0.4280 | 0.6043 | 0.7300 | 0.9023 | 0.9107 |
| 2.0 mM AGK | 0.1757 | 0.4577 | 0.7440 | 0.7997 | 1.0263 | 1.0620 |
| 0% FBS | 0.1970 | 0.3873 | 0.4227 | 0.2927 | 0.3200 | 0.2313 |
| Standard deviation (SD, n = 3) | | | | | | |
| 1.1 mM GPP | 0.0169 | 0.0410 | 0.0421 | 0.0190 | 0.1292 | 0.0613 |
| 2.2 mM DGP | 0.0183 | 0.0462 | 0.0541 | 0.0507 | 0.1180 | 0.1310 |
| 2.1 mM GEK | 0.0046 | 0.0269 | 0.0172 | 0.0599 | 0.1270 | 0.1182 |
| 2.0 mM AGK | 0.0081 | 0.0229 | 0.0471 | 0.0318 | 0.1376 | 0.1074 |
| 0% FBS | 0.0010 | 0.0104 | 0.0150 | 0.0153 | 0.0140 | 0.0320 |

From Table 12 and FIG. 12, it was found that, under the above-mentioned testing conditions, the addition of the peptide solution increased the cell number as days passed as compared to the system without the addition.

(Cell Growth Test of Each Peptide on Coating Agent for 3 Days)

Peptides having the sequences of Gly-Glu-Lys (GEK) and Asp-Gly-Pro (DGP) were synthesized to prepare each peptide solution such that the concentration was a concentration at which the cell number increased the most within a range of 0 mM to 5 mM. In other words, Gly-Glu-Lys (GEK) was adjusted to 21 mM, and Asp-Gly-Pro (DGP) was adjusted to 22 mM, and an amount of 1/10 of the total culture medium volume was added to each well immediately before the cell culture test such that final concentrations were 2.1 mM and 2.2 mM, respectively.

Poly-L-lysine (Peptide Institute, Inc., Poly-L-Lysine Hydrochloride, code: 3075) was prepared to 0.1 mg/mL, and 200 μL was dispensed into each well of a 24-well plate, which was left to stand in an incubator at 37° C. for 2 hours. After removing the residual liquid with an aspirator, rinsing was performed with distilled water, irradiation was performed with a UV lamp in a clean bench without a lid, and drying was performed overnight to sterilize. A cell suspension prepared such that CHO-K1 (RIKEN BioResource Research Center, cell number: RCB2330) was at $4\times10^4$ cells/mL was seeded in a 24-well plate at 500 μL/well and cultured in an incubator at 37° C. and 5% $CO_2$ for 24 hours. As a culture medium, an MEMα culture medium (Gibco) containing 10% FBS was used.

After removing the culture medium from each well and washing with the MEMα culture medium (500 μL), 450 μL of a new MEMα culture medium was dispensed into each well, and each peptide solution (50 μL) was added (total 500 μL/well) to perform culture for 3 days. The cells were recovered to count the cell number. A similar culture test was performed using a system containing neither peptide nor FBS as a comparative sample.

The culture medium in each well was recovered in a 1.5 mL tube to be rinsed with 200 μL of MEMα, and the rinsed liquid was also recovered in the same 1.5 mL tube. Thereafter, 100 μL of trypsin was added and incubated for 3 minutes. After rinsing with 300 μL of MEMα containing 10% FBS, the rinsed liquid was also recovered in the same 1.5 mL tube. After rinsing again with 200 μL of MEMα containing 10% FBS, the rinsed liquid was also recovered in the same 1.5 mL tube.

A centrifugation operation was performed on the cells recovered in the 1.5 mL tube. The centrifugation conditions were 1,000 rpm, 10 minutes, and 4° C.

The supernatant was removed, and 300 μL of Cold PBS (phosphate buffered saline) was added to perform a centrifugation operation under the same conditions. The present operation was repeated twice.

Suspension was carried out with 100 μL of Binding Buffer, and 2 μL of propidium iodide (PI) was added and stirred in the tube to cause a reaction for 15 minutes at room temperature and with light shielding. Thereafter, the viable cell count and the viability were measured with a flow cytometer.

Figure 13:
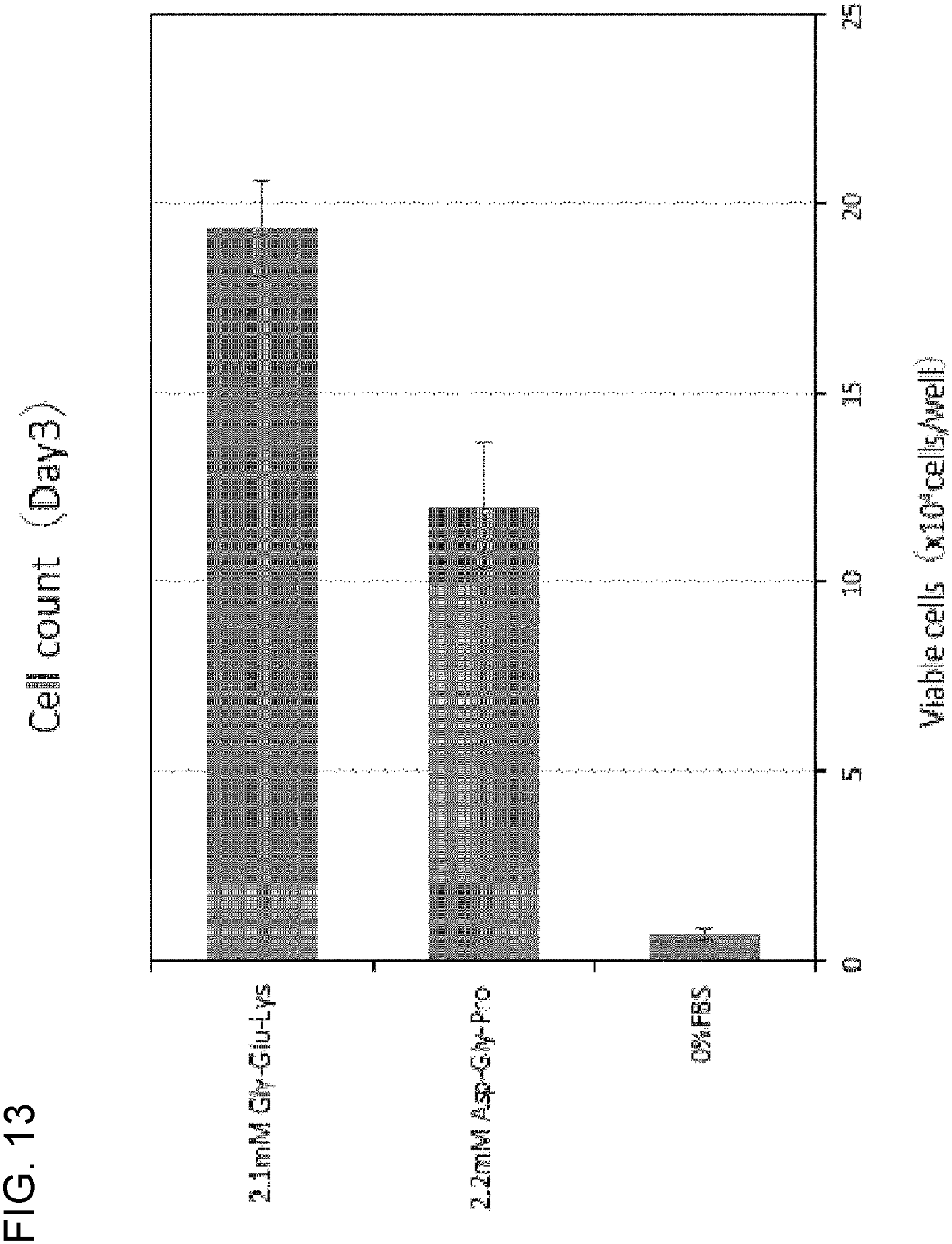
FIG. 13 shows the viable cell count for each tripeptide in a cell growth test for 3 days.
Figure 14:
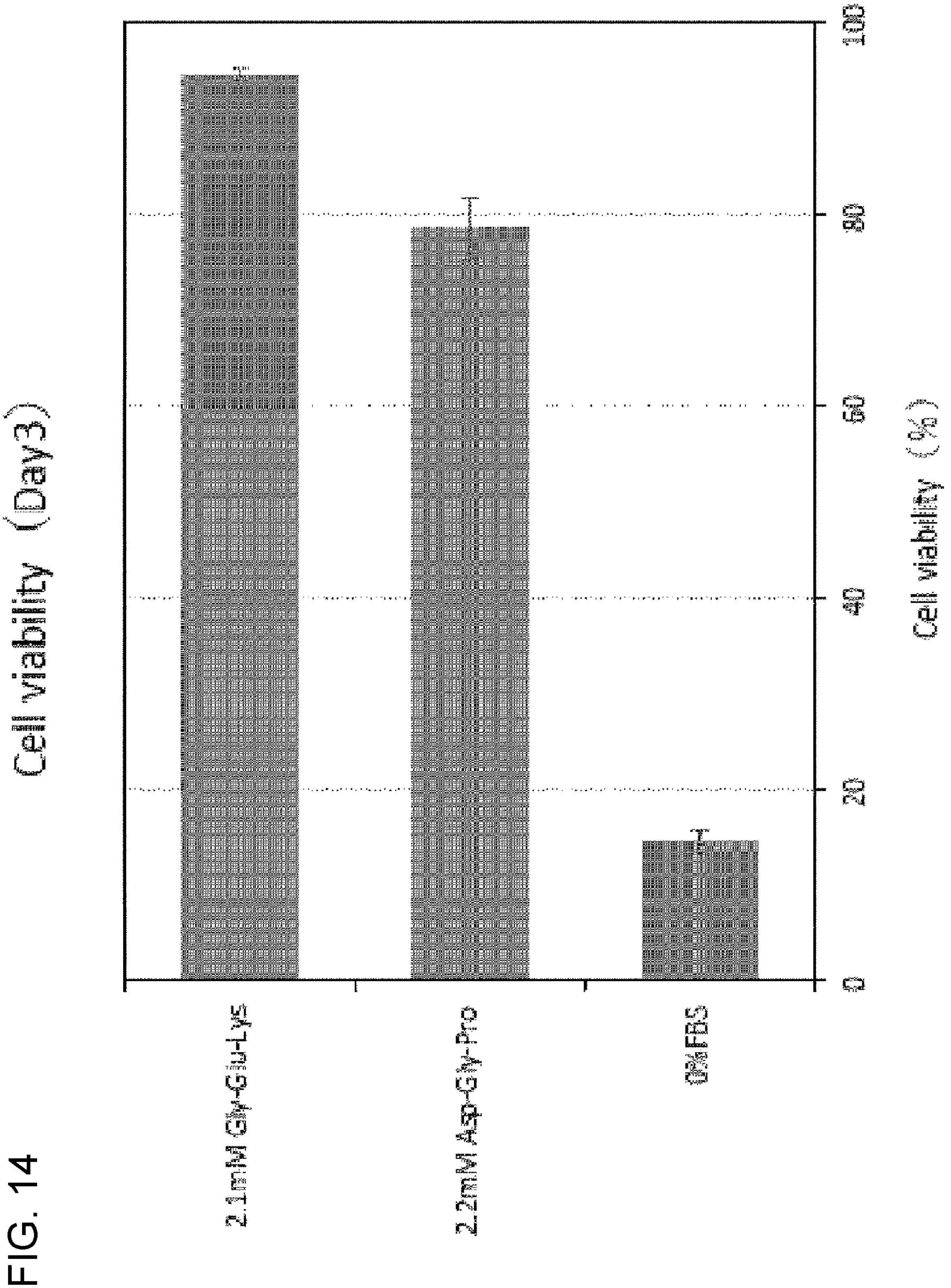
FIG. 14 shows the cell viability for each tripeptide in the cell growth test for 3 days.

The above preparation, culture, and measurement were performed with n=3. Table 13 and FIG. 13 show the viable cell count in each peptide solution, and Table 14 and FIG. 14 show the cell viability in each peptide solution.

TABLE 13

| | Cells | | | | |
|---|---|---|---|---|---|
| cell count ($\times10^4$) | 1 | 2 | 3 | Average | SD |
| 0% FBS | 0.59 | 0.88 | 0.64 | 0.71 | 0.16 |
| 2.2 mM Asp-Gly-Pro | 11.69 | 10.47 | 13.82 | 11.99 | 1.70 |
| 2.1 mM Gly-Glu-Lys | 17.94 | 19.72 | 20.39 | 19.35 | 1.26 |

TABLE 14

| | Viability | | | | |
|---|---|---|---|---|---|
| | 1 | 2 | 3 | Average | SD |
| 0% FBS | 13.1 | 15.3 | 15.3 | 14.6 | 1.3 |
| 2.2 mM Asp-Gly-Pro | 77.9 | 75.6 | 82.0 | 78.5 | 3.2 |
| 2.1 mM Gly-Glu-Lys | 94.7 | 95.1 | 93.8 | 94.5 | 0.7 |

From Table 13, Table 14, FIG. 13, and FIG. 14, it was found that the viable cell count increased and the cell viability was also higher in the peptide culture on a coating agent for 3 days under the above-mentioned testing conditions, as compared to the system to which the peptides were not added.

(Cell Growth Test of Each Peptide on Coating Agent for 5 Days)

Peptides having the sequences of Asp-Gly-Pro (DGP), Ala-Gly-Lys (AGK), Gly-Glu-Lys (GEK), and Gly-Gly-Gly (GGG) were synthesized to prepare each peptide solution such that the concentration was a concentration at which the cell number increased the most within a range of 0 mM to 5 mM. In other words, Asp-Gly-Pro (DGP) was adjusted to 22 mM, Ala-Gly-Lys (AGK) was adjusted to 20 mM, Gly-Glu-Lys (GEK) was adjusted to 21 mM, and Gly-Gly-Gly (GGG) was adjusted to 25 mM, and an amount of 1/10 of the total culture medium volume was added to each well immediately before the cell culture test such that final concentrations were 2.2 mM, 2.0 mM, 2.1 mM, and 2.5 mM, respectively. Poly-L-lysine (Peptide Institute, Inc., Poly-L-Lysine Hydrochloride, code: 3075) was prepared to 0.1 mg/mL, and 200 μL was dispensed into each well of a 24-well plate, which was left to stand in an incubator at 37° C. for 2 hours. After removing the residual liquid with an aspirator, rinsing was performed with distilled water, irradiation was performed with a UV lamp in a clean bench without a lid, and drying was performed overnight to sterilize. A cell suspension prepared such that CHO-K1 (RIKEN BioResource Research Center, cell number: RCB2330) was at $4\times10^4$ cells/mL was seeded in each well of a 24-well plate at 500 μL/well and cultured in an incubator at 37° C. and 5% $CO_2$ for 24 hours. As a culture medium, an MEMα culture medium (Gibco) containing 10% FBS was used.

After removing the culture medium from each well and washing with the MEMα culture medium (500 μL), 450 μL of a new MEMα culture medium was dispensed into each well, and each peptide solution (50 μL) was added (total 500 μL/well) to perform culture for 5 days. The cells were recovered to count the cell number. A similar culture test was performed using a system containing neither peptide nor FBS as a comparative sample.

The culture medium in each well was recovered in a 1.5 mL tube to be rinsed with 200 μL of MEMα, and the rinsed liquid was also recovered in the same 1.5 mL tube. Thereafter, 100 μL of trypsin was added and incubated for 3 minutes. After rinsing with 300 μL of MEMα containing 10% FBS, the rinsed liquid was also recovered in the same 1.5 mL tube. After rinsing again with 200 μL of MEMα containing 10% FBS, the rinsed liquid was also recovered in the same 1.5 mL tube.

A centrifugation operation was performed on the cells recovered in the 1.5 mL tube. The centrifugation conditions were 1,000 rpm, 10 minutes, and 4° C.

The supernatant was removed, and 300 μL of Cold PBS (phosphate buffered saline) was added to perform a centrifugation operation under the same conditions. The present operation was repeated twice.

Suspension was carried out with 100 μL of Binding Buffer, and 2 μL of propidium iodide (PI) was added and stirred in the tube to cause a reaction for 15 minutes at room temperature and with light shielding. Thereafter, the viable cell count and the cell viability were measured with a flow cytometer.

Figure 15:
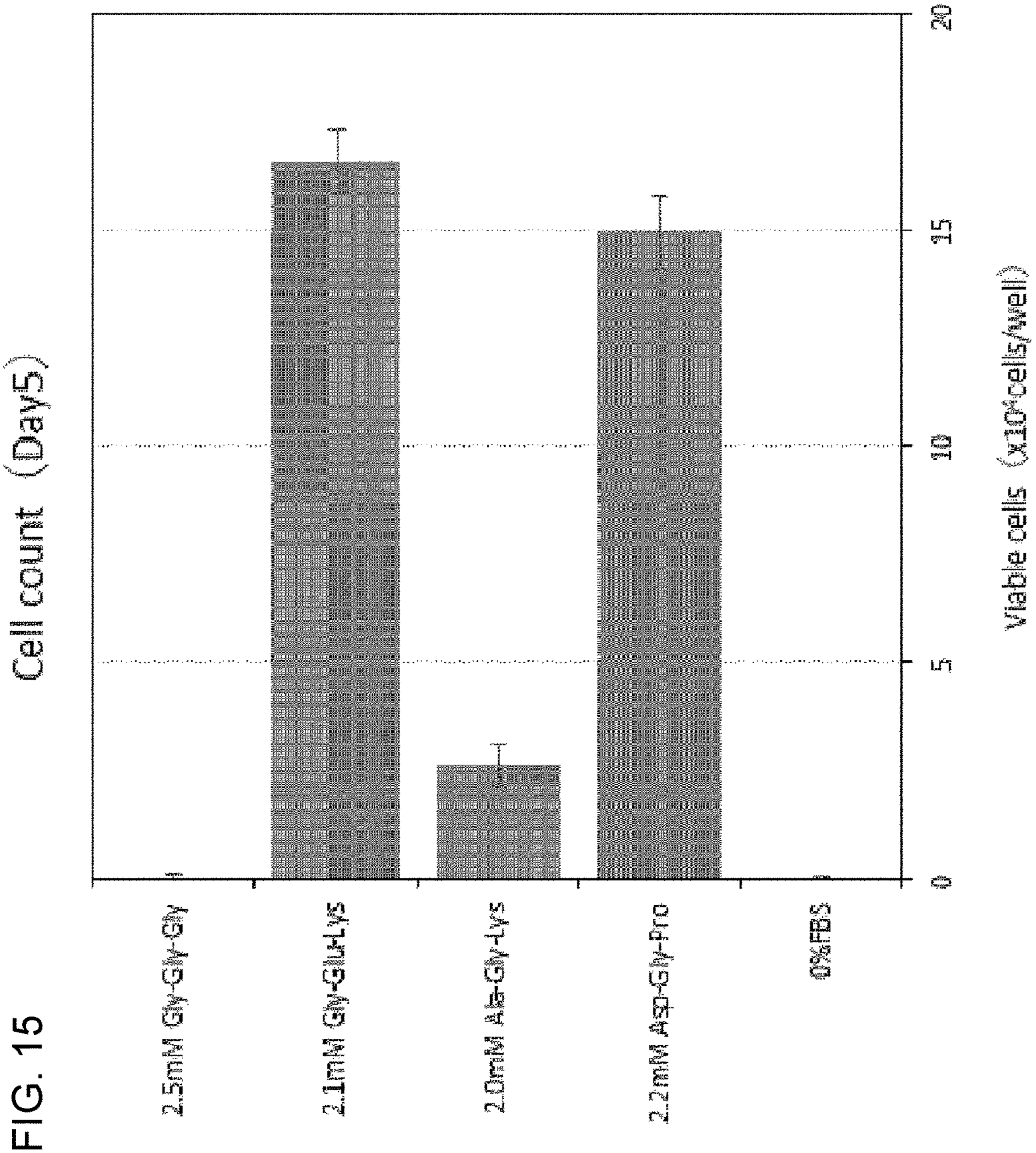
FIG. 15 shows the viable cell count for each tripeptide in a cell growth test for 5 days.
Figure 16:
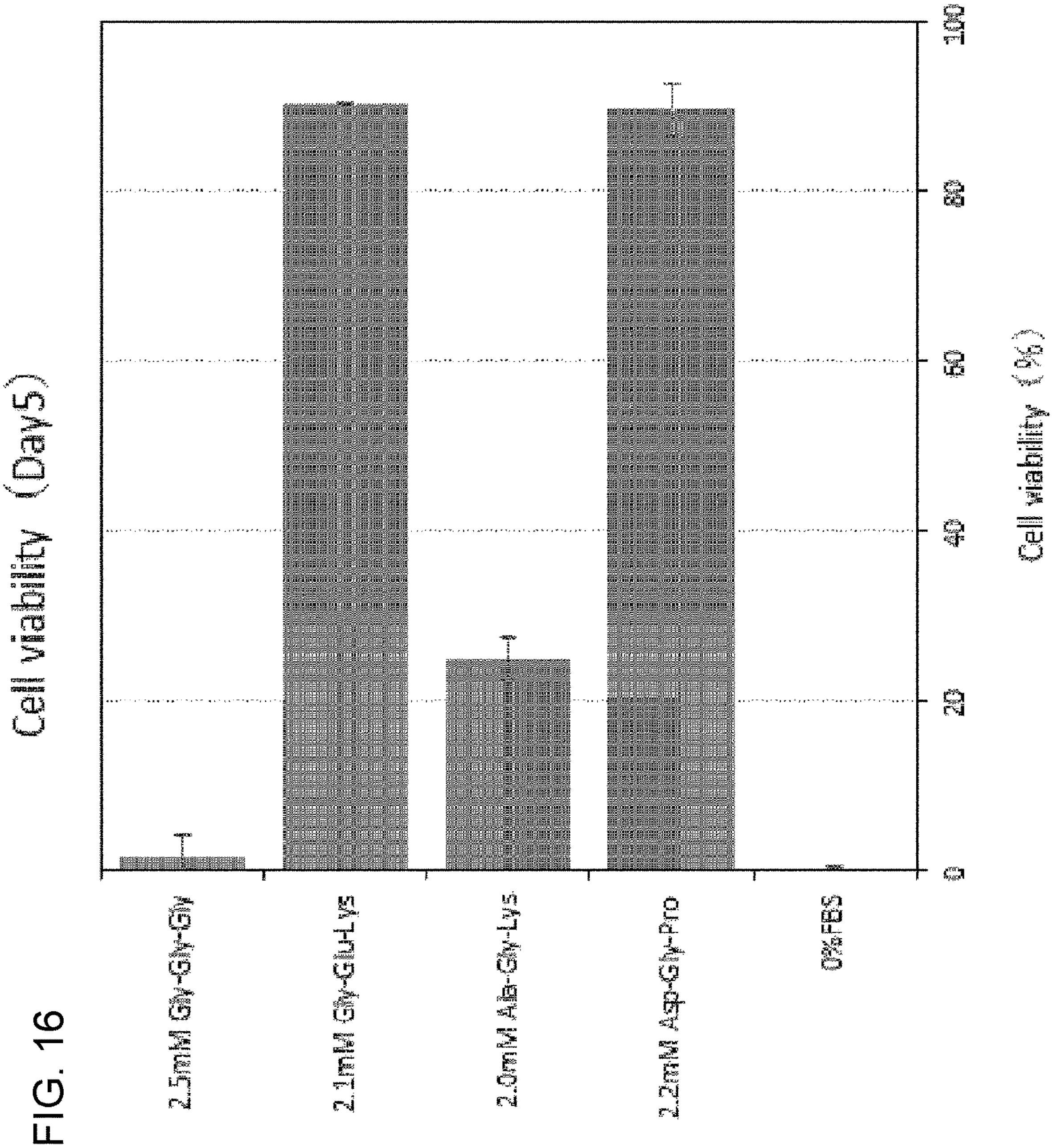
FIG. 16 shows the cell viability for each tripeptide in the cell growth test for 5 days.

The above preparation, culture, and measurement were performed with n=3. Table 15 and FIG. 15 show the viable cell count in each peptide solution, and Table 16 and FIG. 16 show the cell viability in each peptide solution.

TABLE 15

| | Cells | | | | |
|---|---|---|---|---|---|
| cell count ($\times10^4$) | 1 | 2 | 3 | Mean | SD |
| 0% FBS | 0.0070 | 0.0100 | 0.0030 | 0.0067 | 0.0035 |
| 2.2 mM Asp-Gly-Pro | 15.8220 | 14.8590 | 14.1250 | 14.9353 | 0.8511 |

TABLE 15-continued

| | Cells | | | | |
|---|---|---|---|---|---|
| cell count ($\times10^4$) | 1 | 2 | 3 | Mean | SD |
| 2.0 mM Ala-Gly-Lys | 2.6860 | 3.0605 | 2.1185 | 2.6217 | 0.4743 |
| 2.1 mM Gly-Glu-Lys | 15.7190 | 16.9875 | 17.0425 | 16.5830 | 0.7488 |
| 2.5 mM Gly-Gly-Gly | 0.1360 | 0.0080 | 0.0065 | 0.0502 | 0.0743 |

TABLE 16

| | Viability | | | | |
|---|---|---|---|---|---|
| | 1 | 2 | 3 | Mean | SD |
| 0% FBS | 0.4 | 0.4 | 0.3 | 0.4 | 0.1 |
| 2.2 mM Asp-Gly-Pro | 91.5 | 91.2 | 86.0 | 89.6 | 3.1 |
| 2.0 mM Ala-Gly-Lys | 26.4 | 26.4 | 22.1 | 25.0 | 2.5 |
| 2.1 mM Gly-Glu-Lys | 90.2 | 90.3 | 90.5 | 90.3 | 0.2 |
| 2.5 mM Gly-Gly-Gly | 4.45 | 0.31 | 0.21 | 1.7 | 2.4 |

From Table 15, Table 16, FIG. 15, and FIG. 16, it was found that, except GGG, the cell number increased and the cell viability was also higher in the peptide culture on a coating agent for 5 days under the above-mentioned testing conditions, as compared to the system to which the peptides were not added.

(Cell Growth Test and Protein Production Test on Each Peptide and Combination of Peptides on Coating Agent)

Peptides having the sequences of Gly-Pro-Pro (GPP), Asp-Gly-Pro (DGP), Gly-Glu-Lys (GEK), and Ala-Gly-Lys (AGK) were synthesized to prepare each peptide solution such that the concentration was a concentration at which the cell number increased the most within a range of 0 mM to 5 mM. In other words, Gly-Pro-Pro (GPP) was adjusted to 11 mM, Asp-Gly-Pro (DGP) was adjusted to 22 mM, Gly-Glu-Lys (GEK) was adjusted to 21 mM, and Ala-Gly-Lys (AGK) was adjusted to 20 mM, and an amount of 1/10 of the total culture medium volume was added to each well immediately before the cell culture test such that final concentrations were 1.1 mM, 2.2 mM, 2.1 mM, and 2.0 mM, respectively. Poly-L-lysine (Peptide Institute, Inc., Poly-L-Lysine Hydrochloride, code: 3075) was prepared to 0.1 mg/mL, and 200 μL was dispensed into each well of a 24-well plate, which was left to stand in an incubator at 37° C. for 2 hours. After removing the residual liquid with an aspirator, rinsing was performed with distilled water, irradiation was performed with a UV lamp in a clean bench without a lid, and drying was performed overnight to sterilize. A cell suspension prepared such that CHO DP-12 (ATCC, Cat. No. CRL-12445) was at $2\times10^4$ cells/well and 500 μL was seeded in a 24-well plate and cultured in an incubator at 37° C. and 5% $CO_2$ for 24 hours. As a culture medium, a DMEM basal medium in which 200 nM of methotrexate and 2 μg/mL of insulin were blended in a DMEM culture medium (Gibco) containing 10% FBS was used.

After removing the culture medium from each well and washing with the DMEM basal medium (500 μL), 450 μL of a new DMEM basal medium was dispensed into each well, and each peptide solution (50 μL) was added (total 500 μL/well) to perform culture for 5 days.

As peptides, in addition to single GPP, DGP, GEK, and AGK, combinations of GPP+GEK, GPP+AGK, DGP+GEK, GEK+AGK, DGP+AGK, GPP+GEK+AGK, GPP+DGP+AGK, and GPP+DGP+GEK were used. A similar culture test was performed using a system containing neither peptide nor FBS as a comparative sample.

In order to measure the amount of protein produced, 100 μL of the culture medium supernatant was recovered in a 1.5 mL tube and diluted to quantitatively determine the amount of protein produced by an ELISA method.

In order to recover the cells, the culture medium in each well was recovered in a 1.5 mL tube to be rinsed with 200 μL of the DMEM basal medium, and the rinsed liquid was also recovered in the same 1.5 mL tube. Thereafter, 100 μL of trypsin was added and incubated for 3 minutes. After rinsing with 300 μL of the DMEM basal medium containing 10% FBS, the rinsed liquid was also recovered in the same 1.5 mL tube. After rinsing again with 200 μL of the DMEM basal medium containing 10% FBS, the rinsed liquid was also recovered in the same 1.5 mL tube.

A centrifugation operation was performed on the cells recovered in the 1.5 mL tube. The centrifugation conditions were 1,000 rpm, 10 minutes, and 4° C.

The supernatant was removed, and 300 μL of Cold PBS (phosphate buffered saline) was added to perform a centrifugation operation under the same conditions. The present operation was repeated twice.

Suspension was carried out with 100 μL of Binding Buffer, and 2 μL of propidium iodide (PI) was added and stirred in the tube to cause a reaction for 15 minutes at room temperature and with light shielding. Thereafter, the viable cell count and the cell viability were measured with a flow cytometer.

Figure 17:
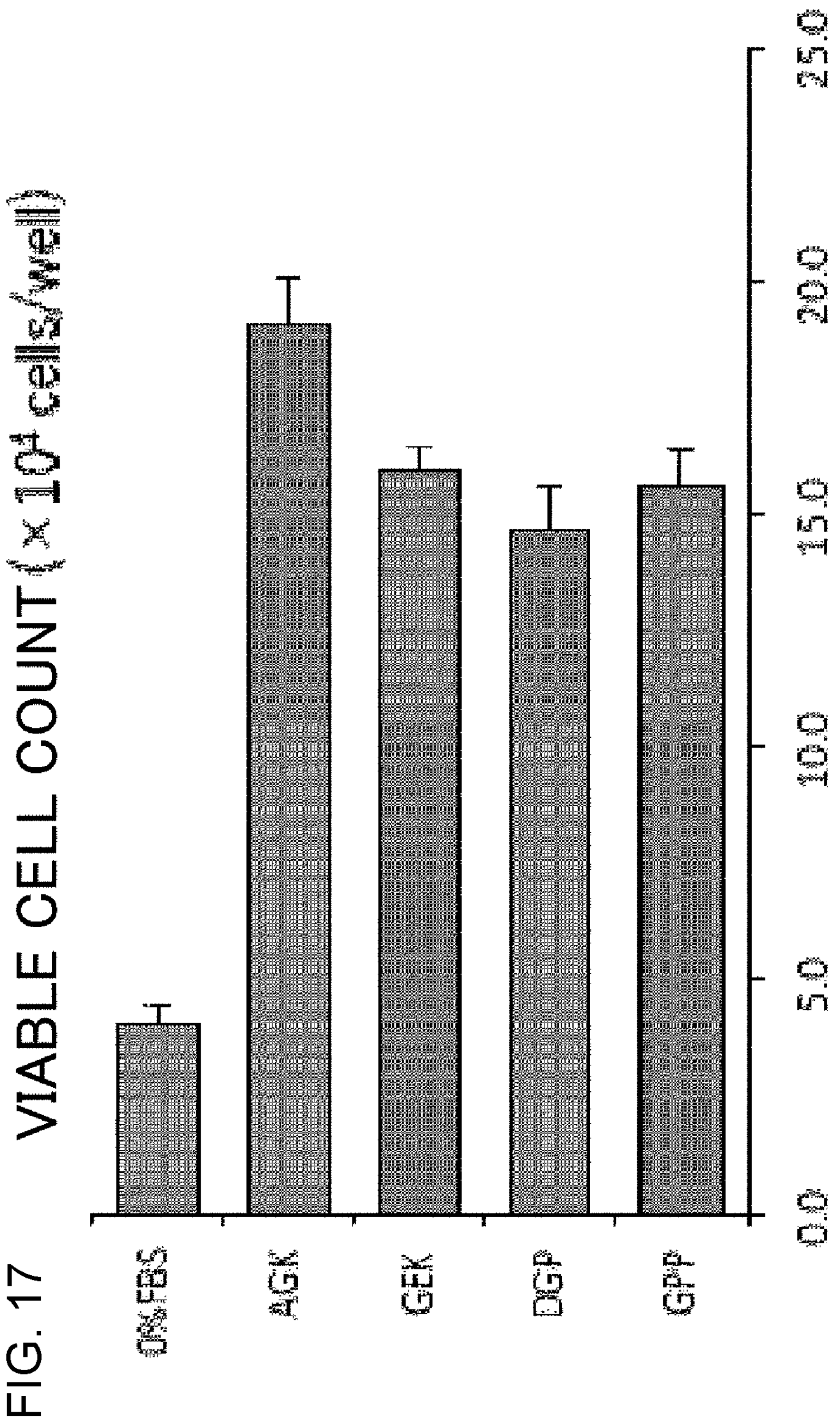
FIG. 17 shows the viable cell count for each tripeptide in a cell growth test of one type of tripeptide.
Figure 18:
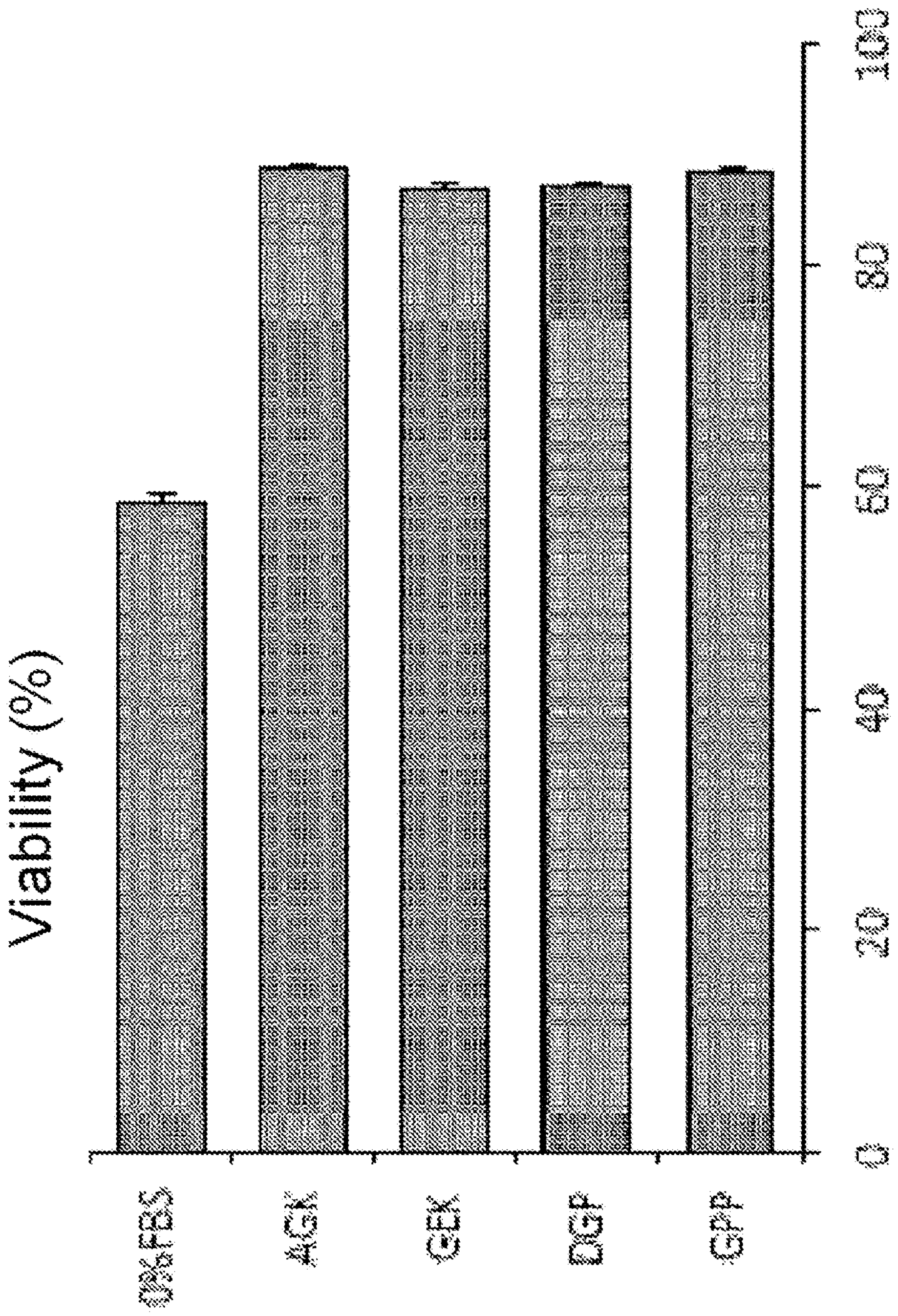
FIG. 18 shows the cell viability for each tripeptide in the cell growth test of one type of tripeptide.
Figure 19:
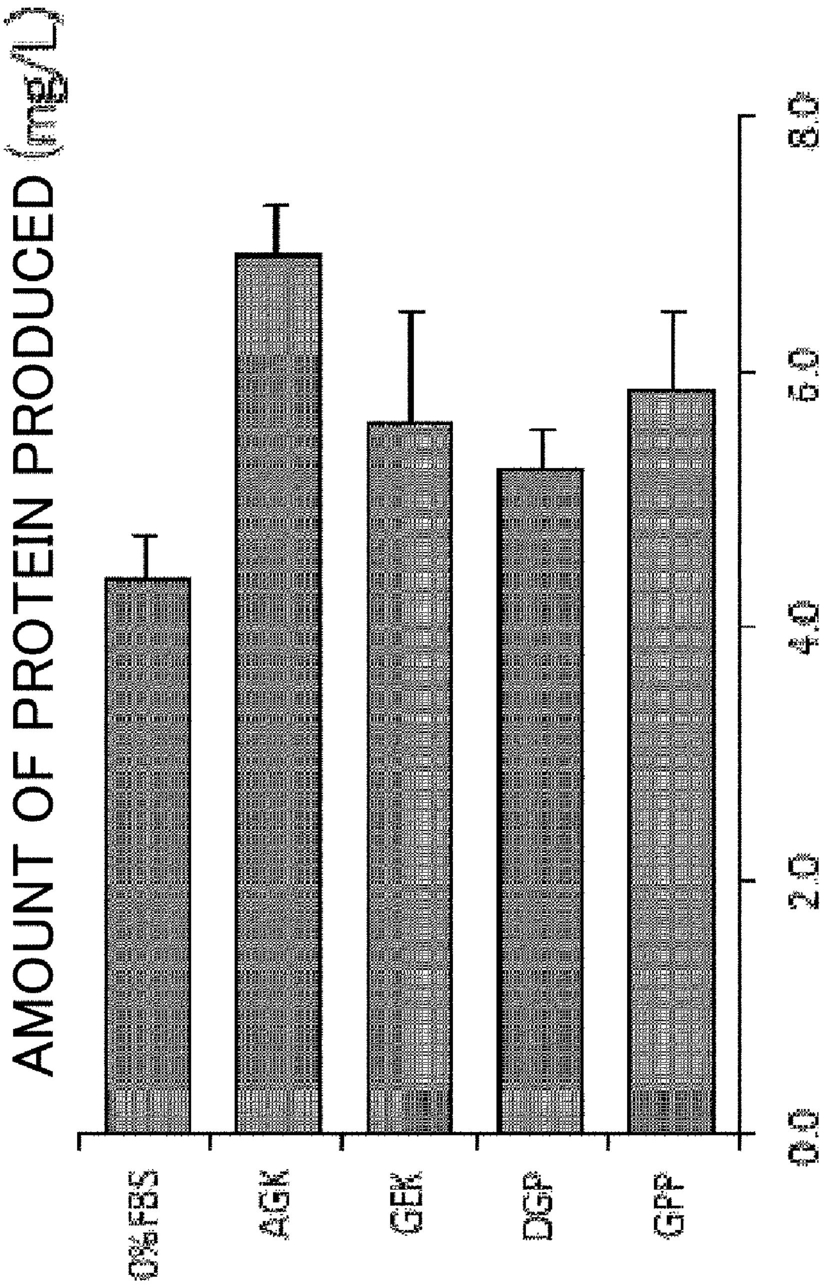
FIG. 19 shows the amount of protein produced for each tripeptide in the cell growth test of one type of tripeptide.
Figure 20:
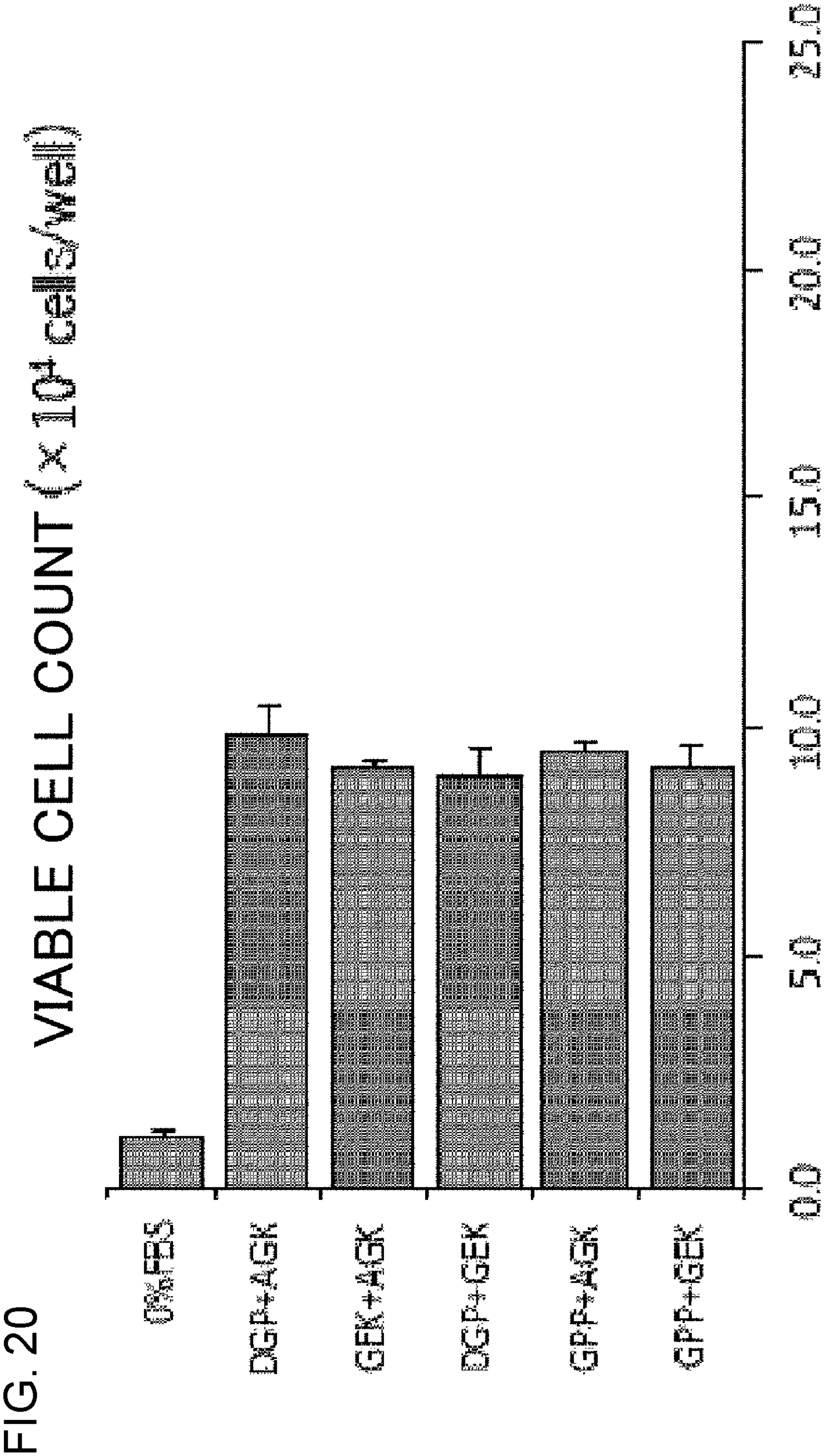
FIG. 20 shows the viable cell count for each combination of the tripeptides in a cell growth test of two types of tripeptides.
Figure 21:
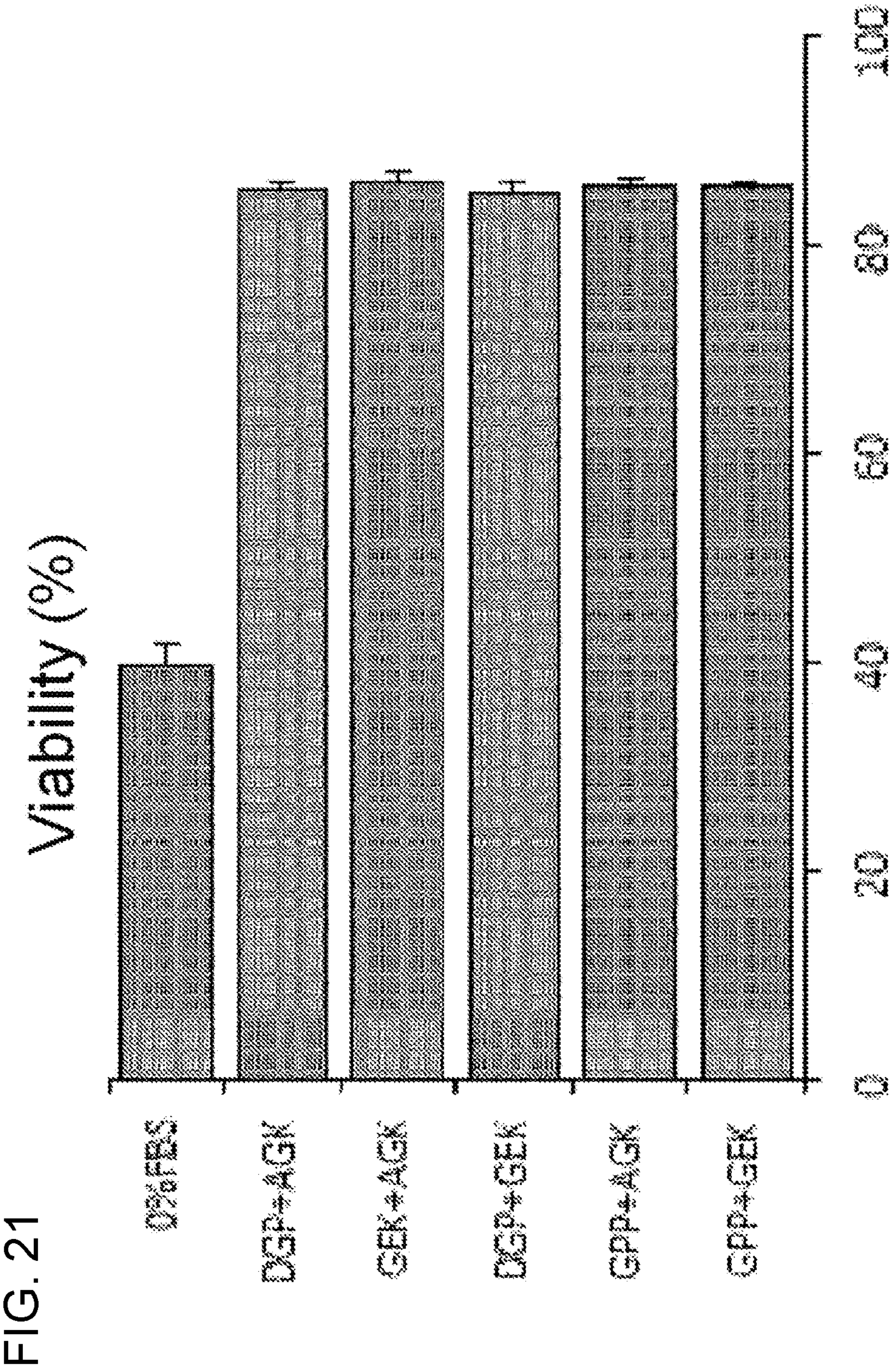
FIG. 21 shows the cell viability for each combination of the tripeptides in the cell growth test of two types of tripeptides.
Figure 22:
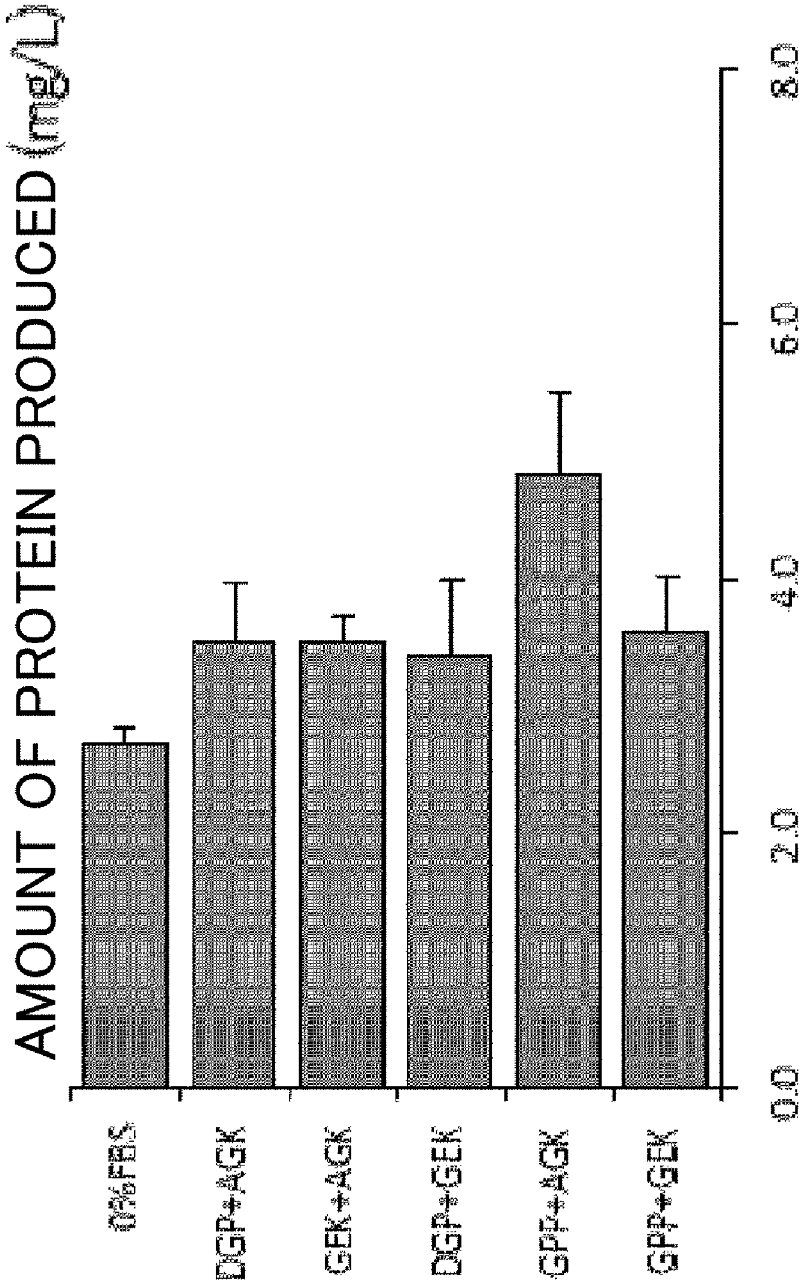
FIG. 22 shows the amount of protein produced for each combination of the tripeptides in the cell growth test of two types of tripeptides.
Figure 23:
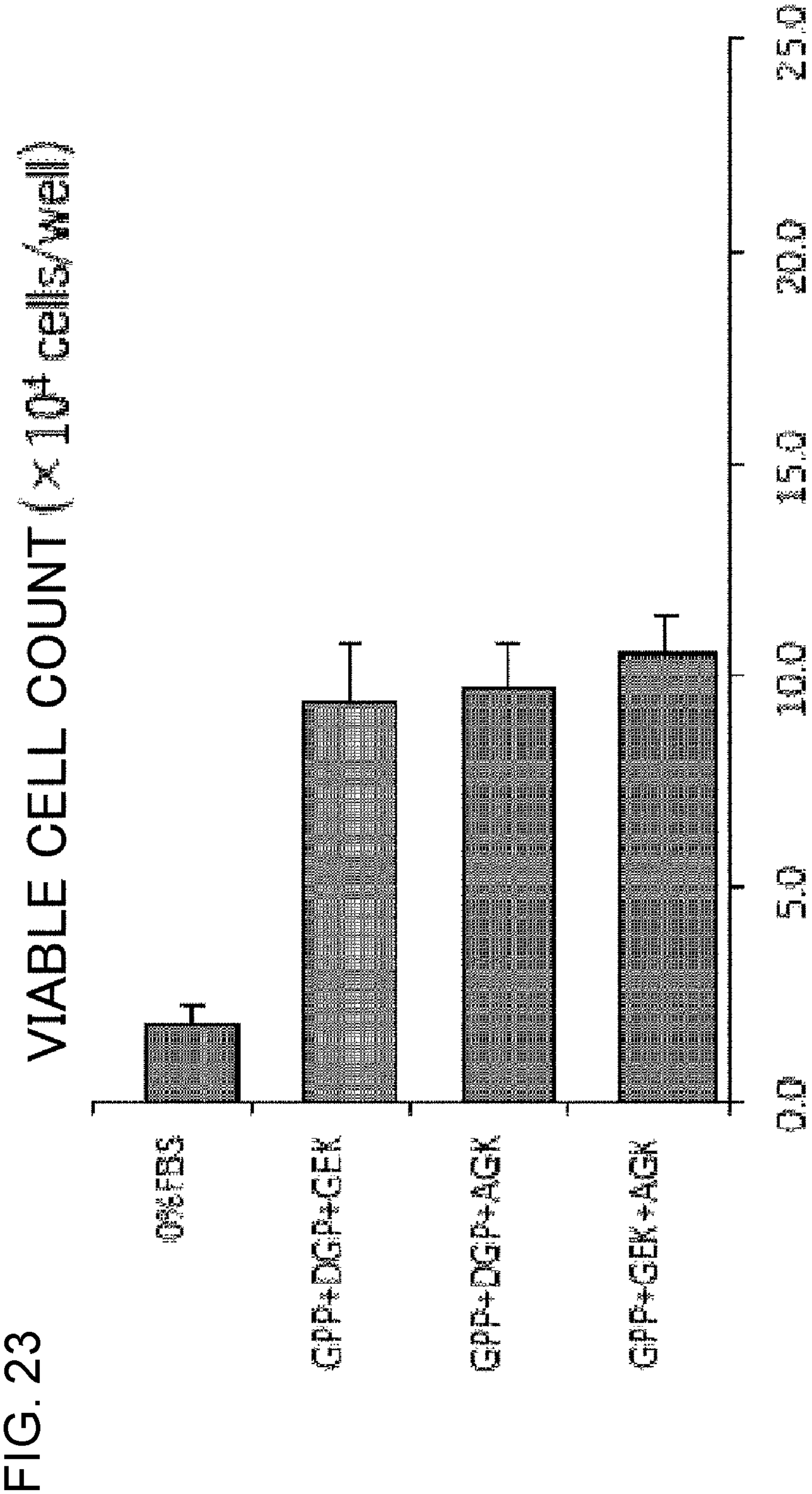
FIG. 23 shows the viable cell count for each combination of the tripeptides in a cell growth test of three types of tripeptides.
Figure 24:
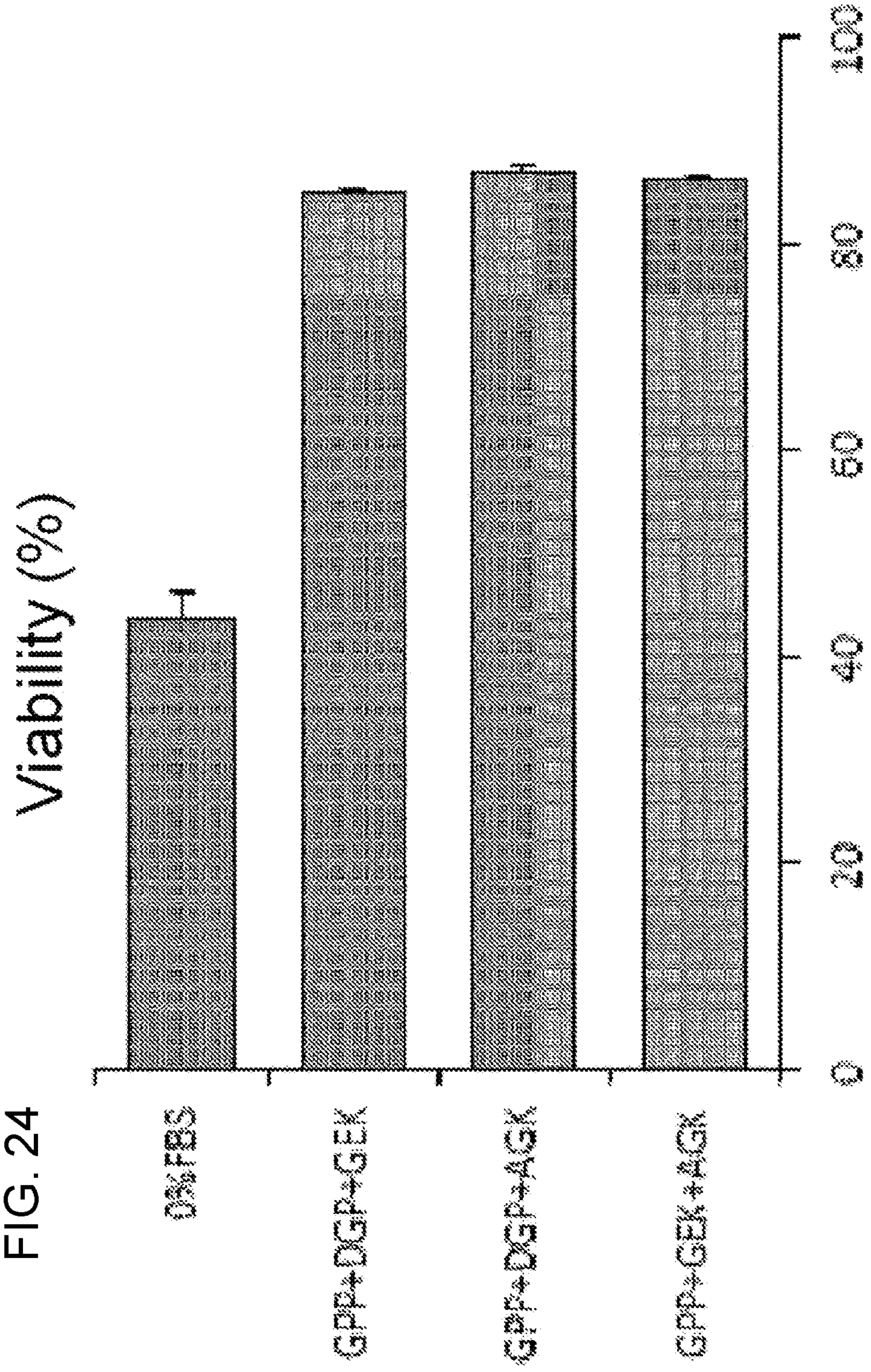
FIG. 24 shows the cell viability for each combination of the tripeptides in the cell growth test of three types of tripeptides.
Figure 25:
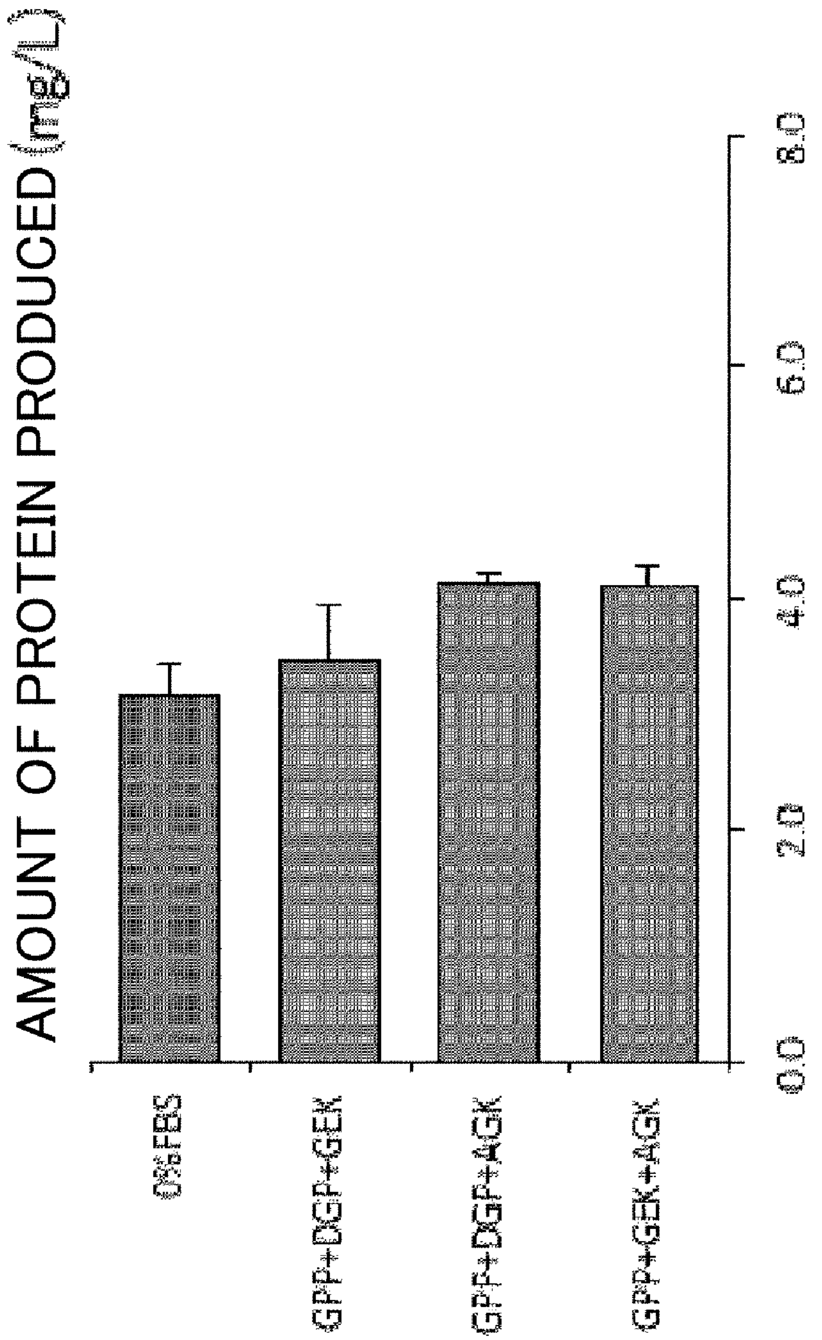
FIG. 25 shows the amount of protein produced for each combination of the tripeptides in the cell growth test of three types of tripeptides.

The above preparation, culture, and measurement were performed with n=3. Table 17, FIG. 17, Table 20, FIG. 20, Table 23, and FIG. 23 show the viable cell count in each peptide solution. Table 18, FIG. 18, Table 21, FIG. 21, Table 24, and FIG. 24 show the cell viability in each peptide solution. Table 19, FIG. 19, Table 22, FIG. 22, Table 25, and FIG. 25 show the amount of protein produced in each peptide solution.

TABLE 17

| Cells | | |
|---|---|---|
| cell count ($\times 10^4$) | Average | SD |
| GPP | 15.5502 | 0.8225 |
| DGP | 14.6333 | 0.9364 |
| GEK | 15.9345 | 0.4884 |
| AGK | 19.0887 | 0.9484 |
| 0% FBS | 4.0250 | 0.4633 |

TABLE 18

| Viability | | | | | |
|---|---|---|---|---|---|
| | 1 | 2 | 3 | Average | SD |
| GPP | 88.9 | 87.9 | 87.9 | 88.2 | 0.6 |
| DGP | 86.3 | 87.3 | 87.2 | 86.9 | 0.6 |
| GEK | 86.5 | 87.4 | 86.7 | 86.9 | 0.5 |
| AGK | 89.0 | 88.5 | 88.1 | 88.5 | 0.5 |
| 0% FBS | 57.8 | 59.5 | 57.9 | 58.4 | 1.0 |

TABLE 19

| Amount of protein produced (mg/L) | | | | | |
|---|---|---|---|---|---|
| | 1 | 2 | 3 | Average | SD |
| GPP | 5.78 | 5.31 | 6.50 | 5.86 | 0.60 |
| DGP | 5.37 | 4.90 | 5.44 | 5.24 | 0.29 |
| GEK | 6.13 | 4.59 | 6.06 | 5.59 | 0.87 |
| AGK | 7.36 | 6.61 | 6.78 | 6.92 | 0.39 |
| 0% FBS | 3.95 | 4.47 | 4.63 | 4.35 | 0.36 |

TABLE 20

| Cells | | |
|---|---|---|
| cell count ($\times 10^4$) | Average | SD |
| GPP + GEK | 9.1175 | 0.5391 |
| GPP + AGK | 9.4750 | 0.1945 |
| DGP + GEK | 8.9357 | 0.6300 |
| GEK + AGK | 9.1192 | 0.1442 |
| DGP + AGK | 9.8113 | 0.6386 |
| 0% FBS | 1.0642 | 0.1651 |

TABLE 21

| Viability | | | | | |
|---|---|---|---|---|---|
| | 1 | 2 | 3 | Average | SD |
| GPP + GEK | 86.3 | 85.7 | 85.1 | 85.7 | 0.6 |
| GPP + AGK | 86.0 | 86.2 | 85.1 | 85.8 | 0.6 |
| DGP + GEK | 84.1 | 85.0 | 86.2 | 85.1 | 1.1 |
| GEK + AGK | 86.0 | 85.4 | 87.3 | 86.2 | 1.0 |
| DGP + AGK | 84.6 | 85.5 | 86.0 | 85.4 | 0.7 |
| 0% FBS | 37.5 | 40.9 | 41.0 | 39.8 | 2.0 |

TABLE 22

| Amount of protein produced (mg/L) | | | | | |
|---|---|---|---|---|---|
| | 1 | 2 | 3 | Average | SD |
| GPP + GEK | 3.70 | 3.95 | 3.06 | 3.57 | 0.46 |
| GPP + AGK | 5.54 | 4.29 | 4.63 | 4.82 | 0.85 |
| DGP + GEK | 4.03 | 2.90 | 3.30 | 3.41 | 0.57 |
| GEK + AGK | 3.32 | 3.44 | 3.72 | 3.49 | 0.21 |
| DGP + AGK | 3.98 | 3.48 | 3.03 | 3.50 | 0.48 |
| 0% FBS | 2.55 | 2.69 | 2.84 | 2.69 | 0.15 |

TABLE 23

| Cells | | |
|---|---|---|
| cell count ($\times 10^4$) | Average | SD |
| GPP + GEK + AGK | 10.5085 | 0.9625 |
| GPP + DGP + AGK | 9.6858 | 1.0850 |
| GPP + DGP + GEK | 9.4232 | 1.3146 |
| 0% FBS | 1.8085 | 0.4705 |

TABLE 24

| Viability | | | | | |
|---|---|---|---|---|---|
| | 1 | 2 | 3 | Average | SD |
| GPP + GEK + AGK | 86.2 | 86.2 | 86.4 | 86.3 | 0.1 |
| GPP + DGP + AGK | 86.4 | 87.5 | 86.9 | 86.9 | 0.6 |
| GPP + DGP + GEK | 84.4 | 85.4 | 84.8 | 84.9 | 0.5 |
| 0% FBS | 40.7 | 44.8 | 45.6 | 43.7 | 2.6 |

TABLE 25

| Amount of protein produced (mg/L) | | | | | |
|---|---|---|---|---|---|
| | 1 | 2 | 3 | Average | SD |
| GPP + GEK + AGK | 4.23 | 3.90 | 4.17 | 4.10 | 0.18 |
| GPP + DGP + AGK | 4.12 | 4.21 | 4.07 | 4.13 | 0.07 |
| GPP + DGP + GEK | 3.06 | 3.30 | 3.98 | 3.45 | 0.48 |
| 0% FBS | 2.87 | 3.16 | 3.41 | 3.15 | 0.27 |

From Tables 17 to 25 and FIGS. 17 to 25, it was found that the addition of a single peptide or a combination of two or more peptides under the above-mentioned testing conditions promoted cell growth and promoted protein production.

(Cell Growth Test and Protein Production Test on Each Peptide—Effects of Adding Vitamins and Nucleic Acids—)

A peptide having the sequence Ala-Gly-Lys (AGK) was synthesized to prepare 1.0 mM and 2.0 mM of peptide solutions.

A cell suspension prepared such that CHO DP-12 (ATCC, Cat. No. CRL-12445) was at $2\times10^4$ cells/mL was seeded in a 24-well plate at $1\times10^4$ cells/well (500 μL) and cultured in an incubator at 37° C. and 5% $CO_2$ for 24 hours. As a culture medium, a DMEM basal medium in which 200 nM of methotrexate and 2 μg/mL of insulin were blended in a DMEM culture medium (Gibco) containing 10% FBS was used.

After removing the culture medium from each well and washing with the DMEM basal medium (500 μL), each peptide solution (500 μL) was dispensed to each well (total 500 μL/well) to perform culture for 5 days.

After replacing each culture medium with an evaluation medium of the following test section, culture was performed in an incubator at 37° C. and 5% $CO_2$ for 5 days.

<Evaluation Medium>

DMEM basal medium

AGK (1 mM)+DMEM basal medium

AGK (2 mM)+DMEM basal medium

Medium supplemented with vitamins and nucleic acids (DMEM basal medium+vitamin+nucleic acid)

AGK (1 mM)+medium supplemented with vitamins and nucleic acids

AGK (2 mM)+medium supplemented with vitamins and nucleic acids

After 5 days of culture, the total amount of the culture medium in each well of the 24-well plate was recovered, a centrifugation operation (5,000 rpm, for 5 minutes) was performed, and the supernatant was separately recovered to measure the amount of produced protein by ELISA.

The composition of the above-mentioned vitamins and nucleic acids is shown in Table 26.

TABLE 26

| Vitamin | (Final concentration of each component) | Nucleic acid | (Final concentration of each component) |
|---|---|---|---|
| Choline chloride | 4.155 mg/L | Xanthine | 0.9 mg/L |
| Niacinamide | 0.276 mg/L | Hypoxanthine | 1.8 mg/L |
| D-pantothenic acid hemicalcium salt | 45.8 μg/L | Uridine | 3.6 mg/L |
| Folic acid | 3.6 μg/L | Guanine hydrochloride | 2.4 mg/L |
| Cyanocobalamin | 0.8 μg/L | Inosine | 4.9 mg/L |
| Pyridoxal hydrochloride | 12.2 μg/L | Guanosine | 3.8 mg/L |
| Riboflavin | 13.8 μg/L | Cytidine | 0.4 mg/L |
| Biotin | 0.8 μg/L | Thymidine | 0.5 mg/L |
| Myo-inositol | 0.73 mg/L | Adenine | 0.8 mg/L |

The cells adhered to the wells after recovering the culture medium were detached by trypsin treatment and suspended again in the DMEM basal medium containing 10% FBS to measure the viable cell count and the viability by a trypan blue staining method using a cell counter.

The above preparation, culture, and measurement were performed with n=3. Table 27 shows the viable cell count, the cell viability, the amount of protein produced in each evaluation medium, and FIG. 26 shows the viable cell count and the amount of protein produced.

TABLE 27

| Test section | Viable cell count ($\times 10^4$cells/well) | Standard deviation ($\times 10^4$cells/well) | Viability (%) | Standard deviation (%) | Amount of protein produced (mg/L) | Standard deviation (mg/L) |
|---|---|---|---|---|---|---|
| Basal medium | 2.61 | 0.43 | 33 | 10 | 4.68 | 0.4 |
| 1 mM AGK | 11.97 | 2.00 | 65 | 8 | 7.5 | 0.6 |
| 2 mM AGK | 11.73 | 1.53 | 65 | 2 | 7.4 | 0.4 |
| Basal medium (Vitamin + Nucleic acid) | 1.17 | 0.43 | 17 | 2 | 4.36 | 0.3 |
| 1 mM AGK(Vitamin + Nucleic acid) | 34.65 | 6.10 | 88 | 2 | 15.74 | 3.6 |
| 2 mM AGK(Vitamin + Nucleic acid) | 47.07 | 8.50 | 89 | 2 | 14.34 | 2.4 |

Figure 26:
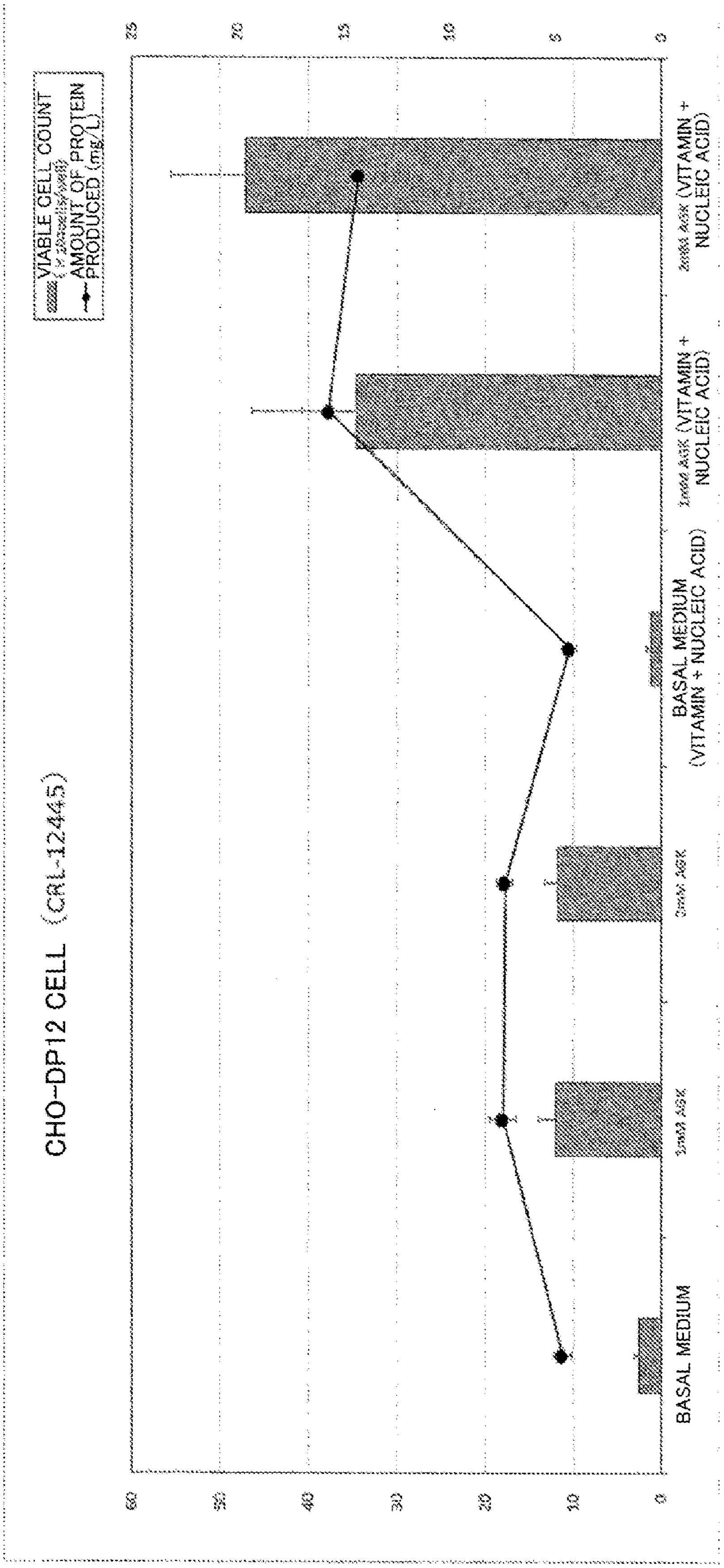
FIG. 26 shows the viable cell count of AGK cells and the amount of protein produced in a cell growth test with the addition of vitamins and nucleic acids.

From Table 27 and FIG. 26, it was found that, under the above-mentioned testing conditions, the addition of peptides to the basal medium increased both the viable cell count and the amount of protein produced, and the further addition of vitamins and nucleic acids further promoted both cell growth and protein production.

(Cell Growth Test and Protein Production Test when Peptide was Added to Total Synthesis Medium)

A peptide having the sequence of Gly-Glu-Lys (GEK) was synthesized to prepare peptide solutions at the concentrations of 0 mM, 2.6 mM, 5.1 mM, 10 mM, 20.5 mM, and 41 mM, and an amount of 1/10 of the total culture medium volume was added to each well immediately before the cell culture test such that final concentrations were 0 mM, 0.26 mM, 0.51 mM, 1.0 mM, 2.05 mM, and 4.1 mM, respectively. In the present test, CHO DP-12 (ATCC, Cat. No. CRL-12445) acclimated to an ASF104 basal medium in which 200 nM of methotrexate and 2 μg/mL of insulin were blended in an ASF104 culture medium (Ajinomoto Co., Inc.), which is a total synthesis medium for CHO, was used. A cell suspension prepared such that a cell concentration was $4\times10^4$ cells/mL was seeded in a 24-well plate at 450 μL/well and cultured in an incubator at 37° C. and 5% $CO_2$ for 24 hours. As a culture medium, an ASF104 basal medium in which 200 nM of methotrexate and 2 μg/mL of insulin were blended in an ASF104 culture medium (Ajinomoto Co., Inc.), which is a total synthesis medium for CHO, was used.

After 24 hours, 50 μL of the prepared peptide solution was added to each well to perform culture for 5 days. The cells were recovered after culture to count the viable cell count.

<Evaluation Medium>

ASF104 basal medium
GEK (0.26 mM)+ASF104 basal medium
GEK (0.51 mM)+ASF104 basal medium
GEK (1.0 mM)+ASF104 basal medium
GEK (2.05 mM)+ASF104 basal medium
GEK (4.1 mM)+ASF104 basal medium 100 μL of the culture medium supernatant was collected in a 1.5 mL tube to quantitatively determine the amount of protein produced. The supernatant was diluted to measure the amount of protein produced by ELISA.

In order to analyze the cells, the culture medium in each well was recovered in a 1.5 mL tube to be rinsed with 200 μL of PBS, and the rinsed liquid was also recovered in the same 1.5 mL tube. Thereafter, 100 μL of 0.25% trypsin/EDTA was added to perform incubation for 1 minute. 100 μL of a trypsin inhibitor was added to recover in the same 1.5 mL tube. After rinsing with 200 μL of PBS to recover the rinsed liquid in the same 1.5 mL tube, a centrifugation operation was performed. Suspension was performed in 100 μL of PBS to measure the viable cell count and the cell viability by a trypan blue staining method using a cell counter.

Figure 27:
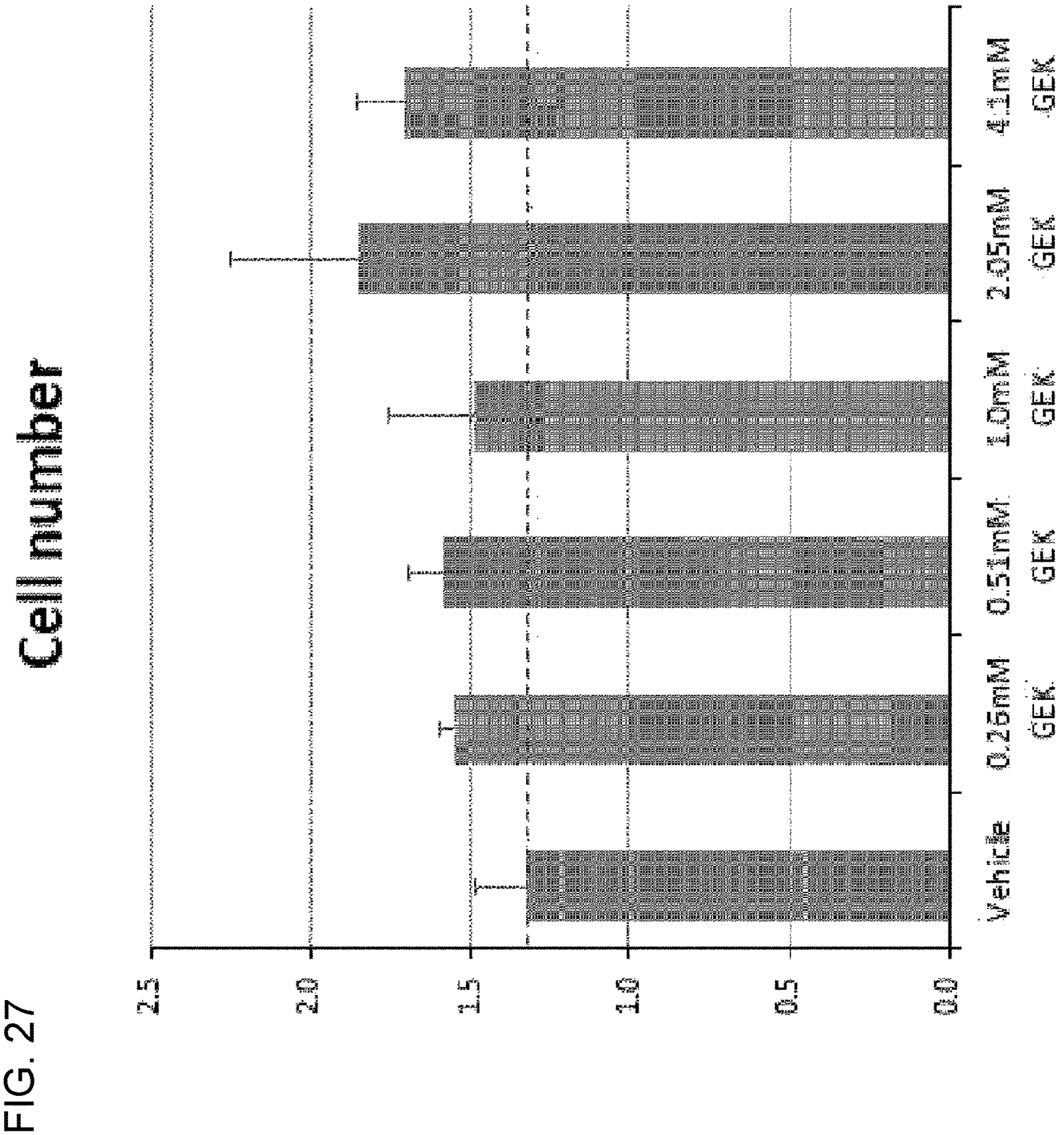
FIG. 27 shows the relationship between the concentration and the viable cell count of GEK in a cell growth test using a total synthesis medium.
Figure 28:
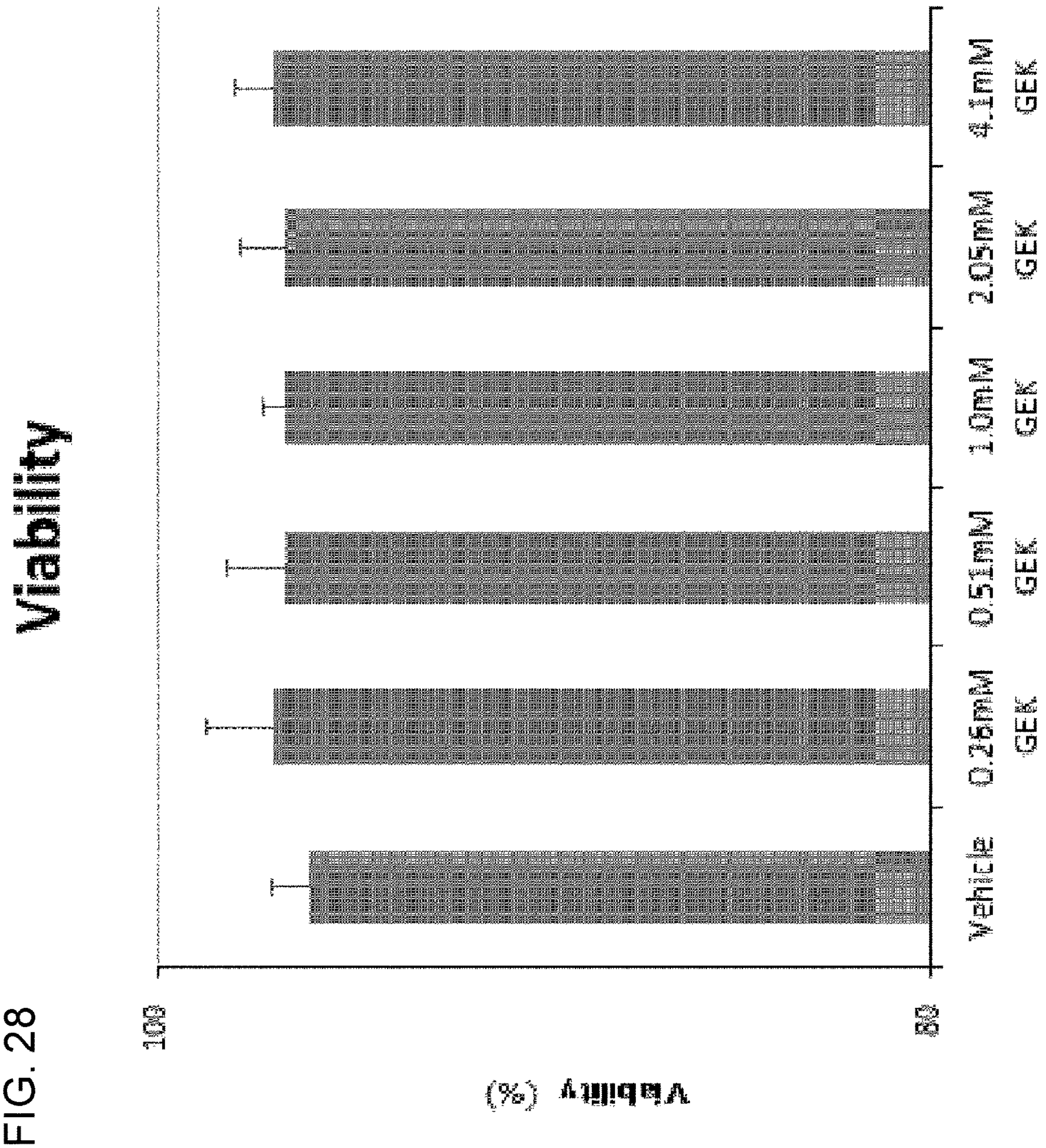
FIG. 28 shows the relationship between the concentration and the cell viability of GEK in the cell growth test using the total synthesis medium.
Figure 29:
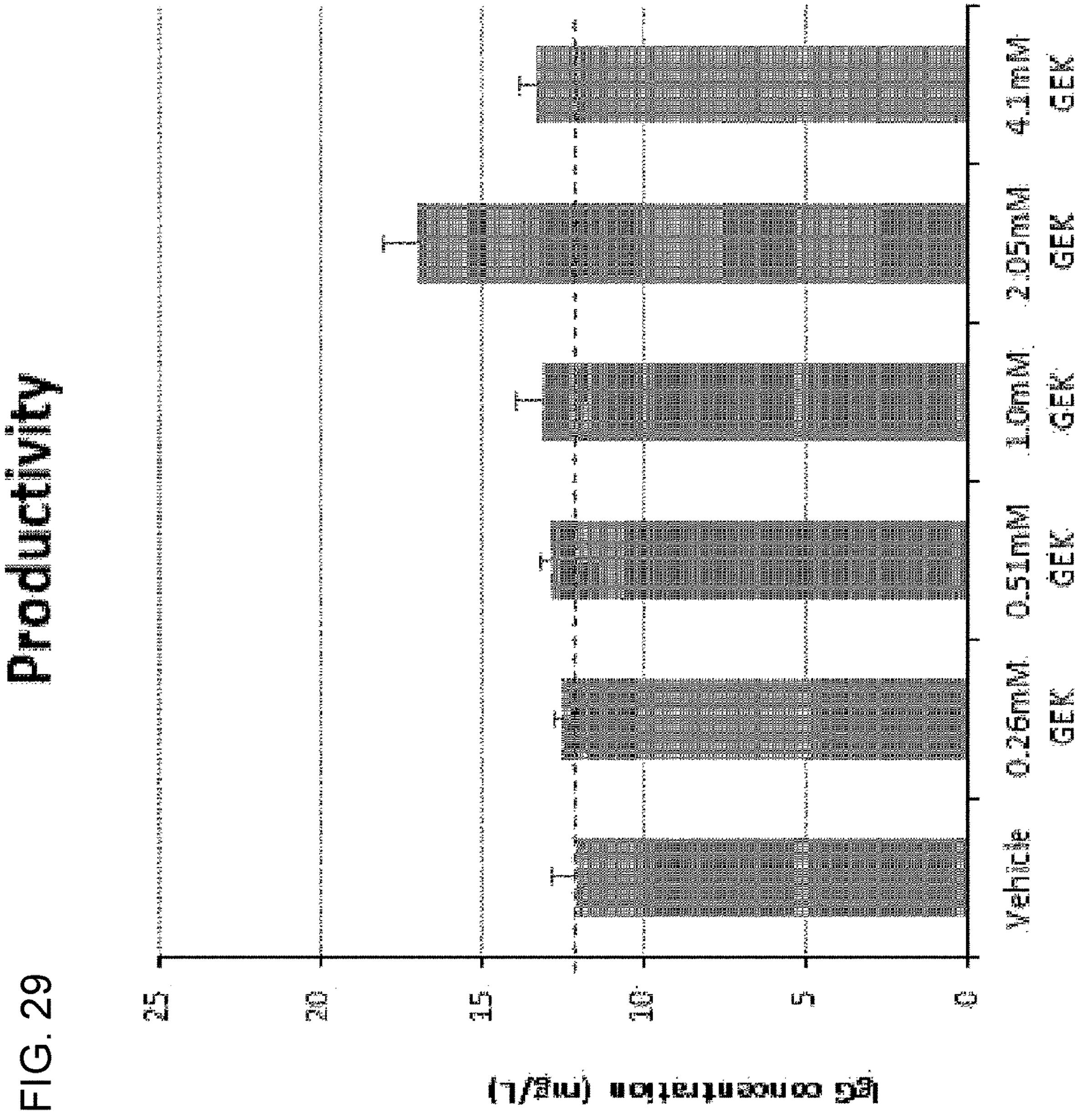
FIG. 29 shows the relationship between the concentration and the amount of protein produced by GEK in the cell growth test using the total synthesis medium.

The above preparation, culture, and measurement were performed with n=3. Table 28 and FIG. 27 show the viable cell count in each peptide solution, Table 29 and FIG. 28 show the cell viability in each peptide solution, and Table 30 and FIG. 29 show the amount of protein produced.

TABLE 28

| | Viable cell count ($\times 10^6$ cells/well) | | | | |
|---|---|---|---|---|---|
| | 1 | 2 | 3 | Average | SD |
| Vehicle | 1.4 | 1.5 | 1.2 | 1.3 | 0.2 |
| 0.26 mM GEK | 1.6 | 1.5 | 1.6 | 1.6 | 0.0 |
| 0.51 mM GEK | 1.5 | 1.7 | 1.6 | 1.6 | 0.2 |
| 1.0 mM GEK | 1.3 | 1.8 | 1.4 | 1.5 | 0.3 |
| 2.05 mM GEK | 1.9 | 2.2 | 1.4 | 1.9 | 0.4 |
| 4.1 mM GEK | 1.8 | 1.8 | 1.5 | 1.7 | 0.1 |

TABLE 29

| | Viability (%) | | | | |
|---|---|---|---|---|---|
| | 1 | 2 | 3 | Average | SD |
| Vehicle | 95 | 96 | 97 | 96.0 | 1.0 |
| 0.26 mM GEK | 96 | 99 | 96 | 97.0 | 1.7 |
| 0.51 mM GEK | 95 | 98 | 97 | 96.7 | 1.5 |
| 1.0 mM GEK | 97 | 97 | 96 | 96.7 | 0.6 |
| 2.05 mM GEK | 96 | 96 | 98 | 96.7 | 1.2 |
| 4.1 mM GEK | 97 | 98 | 96 | 97.0 | 1.0 |

TABLE 30

| | Amount of protein produced (mg/L) | | | | |
|---|---|---|---|---|---|
| | 1 | 2 | 3 | Average | SD |
| Vehicle | 11.4 | 11.9 | 12.8 | 12.0 | 0.7 |
| 0.26 mM GEK | 12.2 | 12.6 | 12.7 | 12.5 | 0.2 |
| 0.51 mM GEK | 12.8 | 13.2 | 12.6 | 12.9 | 0.3 |
| 1.0 mM GEK | 12.4 | 12.8 | 14.1 | 13.1 | 0.9 |
| 2.05 mM GEK | 17.5 | 17.7 | 15.6 | 17.0 | 1.1 |
| 4.1 mM GEK | 13.9 | 13.2 | 12.8 | 13.3 | 0.6 |

From Tables 28 to 30 and FIGS. 27 to 29, it was found that, under the above-mentioned testing conditions, when a GEK peptide was added, the viable cell count increased, the cell viability was similarly high, and the amount of protein produced also tended to increase, indicating that cell growth was promoted and protein production was promoted, as compared to the basal medium in which the commercially available total synthesis medium was used.

(Cell Growth Test and Protein Production Test on GEK and DGP in Floating Cell System)

Peptides having the sequences of Gly-Glu-Lys (GEK) and Asp-Gly-Pro (DGP) were synthesized to prepare peptide solutions of 2.87 mM of Gly-Glu-Lys (GEK), and 1.55 mM of Asp-Gly-Pro (DGP).

5 mL of each of a DMEM/F12 basal medium, a medium supplemented with vitamins and the like (DMEM/F12 basal medium+a component supplemented with vitamins and the like), and each peptide solution was added to each well of a 24-well (Deep well) cassette of Micro-24 Bioreactor System (manufactured by Nihon Pall Corporation) to perform culture overnight under the conditions of 37° C., pH 7, and a stirring speed of 650 rpm. On the next day, pH calibration was performed, and thereafter 2 mL of the cell suspension prepared at $3.5\times10^5$ cells/mL was added to each well of the 24-well (Deep well) cassette, seeded such that the cell density of the floating cells was $1\times10^5$ cells/mL (7 mL/well), and cultured in the following evaluation medium under culture conditions of 37° C., pH 7, a stirring speed of 650 rpm, and dissolved oxygen of 30%.

<Evaluation Medium>

DMEM/F12 basal medium

Medium supplemented with vitamins and the like (basal medium+component supplemented with vitamins and the like)

GEK (2.05 mM)+medium supplemented with vitamins and the like

DGP (1.11 mM)+medium supplemented with vitamins and the like

As a culture medium, a DMEM/F12 basal medium in which 200 nM of methotrexate, 10 μg/mL of insulin, 5.5 μg/mL of transferrin, 6.7 ng/mL of sodium selenite, 10 μL/mL of Anti-Clumping Agent, and 10 μL/mL of 10% Pluronic F68 were blended in a DMEM/F12 culture medium (Gibco) was used.

As the floating cells used, serum-free floating CHO DP-12 obtained by acclimating CHO DP-12 (ATCC, Cat. No. CRL-12445) to serum-free flotation and subculturing using a 100 mL volume Erlenmeyer flask and with a shaking culture device (Custom Bio Shaker CO2-BR-43FL, TAITEC CORPORATION) under the culture conditions of 37° C., 5% $CO_2$, and a stirring speed of 125 rpm was used.

Table 31 shows the above-mentioned component supplemented with vitamins and the like.

TABLE 31

| | Component | (Final concentrationof each component) |
|---|---|---|
| Vitamin | Choline chloride | 20.775 mg/L |
| | Niacinamide | 1.38 mg/L |
| | D-pantothenic acid hemicalcium salt | 229 μg/L |
| | Folic acid | 18 μg/L |
| | Cyanocobalamin | 4 μg/L |
| | Pyridoxal hydrochloride | 61 μg/L |
| | Riboflavin | 69 μg/L |
| | Biotin | 4 μg/L |
| | Myo-inositol | 3.65 mg/L |
| Nucleic acid | Xanthine | 4.5 mg/L |
| | Hypoxanthine | 9 mg/L |
| | Uridine | 18 mg/L |
| | Guanine hydrochloride | 12 mg/L |
| | Inosine | 24.5 mg/L |
| | Guanosine | 19 mg/L |
| | Cytidine | 2 mg/L |
| | Thymidine | 2.5 mg/L |
| | Adenine | 4 mg/L |
| Sugar | Glucose | 220 mg/L |
| Polyamine | Spermidine | 1.75 mg/L |
| | Spermine | 0.5 mg/L |
| | Putrescine | 0.375 mg/L |
| Amino acid | Cystine | 2.4 mg/L |
| | Asparagine | 32.3 mg/L |
| | Aspartic acid | 192.5 mg/L |
| | Serine | 126.35 mg/L |
| | Glycine | 85.35 mg/L |
| | Glutamine | 2.45 mg/L |
| | Cysteine | 22.55 mg/L |
| | Threonine | 128 mg/L |
| | Glutamic acid | 213.35 mg/L |
| | Alanine | 185.15 mg/L |
| | Proline | 30.5 mg/L |
| | Lysine HCl | 277.85 mg/L |
| | Histidine | 120.65 mg/L |
| | Arginine | 216.15 mg/L |
| | Valine | 167.15 mg/L |
| | Methionine | 90.65 mg/L |
| | Tyrosine | 18.35 mg/L |
| | Isoleucine | 138.65 mg/L |
| | Leucine | 246.85 mg/L |
| | Phenylalanine | 120.15 mg/L |
| | tryptophan | 38 mg/L |

After the third day of culture, 200 μL of the culture medium was recovered in a 1.5 mL tube from each well of the 24-well (Deep well) cassette. 50 μL out of this was put in another 1.5 mL tube, and after adding 50 μL of trypan blue to sufficiently suspend, the viable cell count and the viability were measured using a cell counter (Countess II, manufactured by Life Technologies Corporation).

Figure 30:
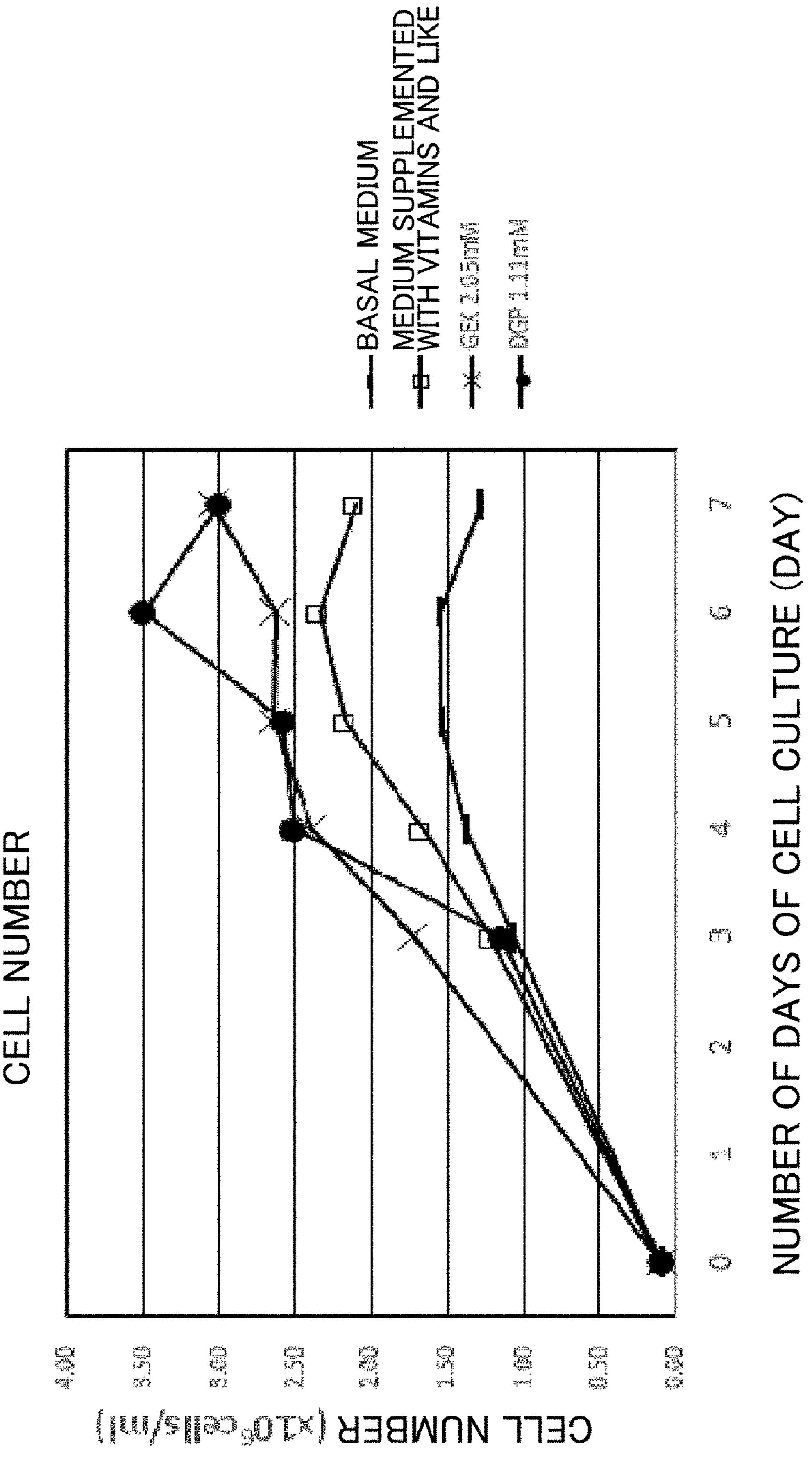
Figure 31:
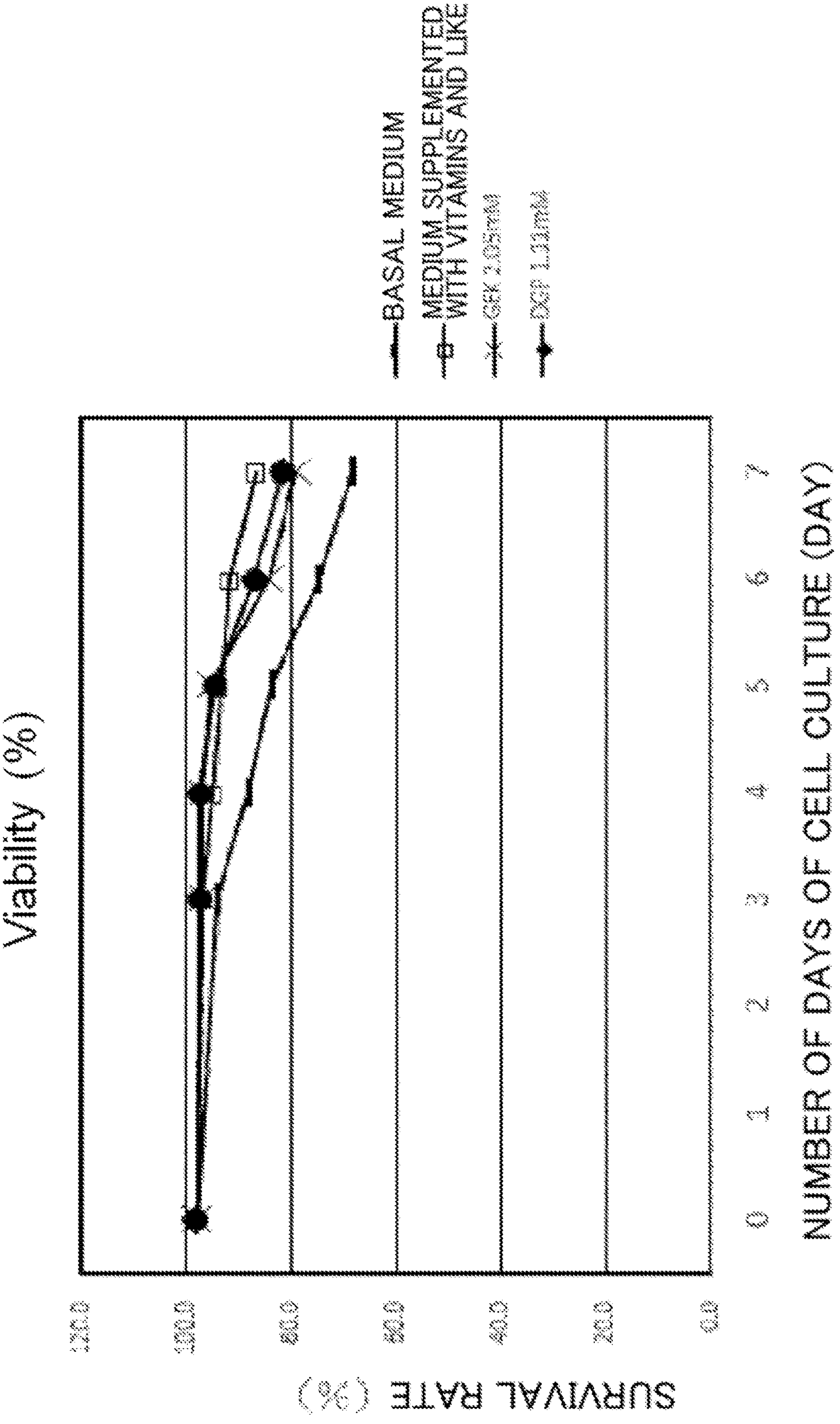

The above preparation, culture, and measurement were performed with n=2 or 3, and Table 32 and FIG. 30 show the viable cell count in each evaluation medium. In addition, Table 33 and FIG. 31 show the viability in each evaluation medium.

TABLE 32

| | Day | | | | | | | |
|---|---|---|---|---|---|---|---|---|
| | 0 | 1 | 2 | 3 | 4 | 5 | 6 | 7 |
| cell number ($\times10^6$cells/ml) | | | | | | | | |
| basal medium | 0.10 | | | 1.07 | 1.39 | 1.55 | 1.55 | 1.29 |
| medium supplemented with vitamins and the like | 0.10 | | | 1.23 | 1.67 | 2.18 | 2.35 | 2.11 |

TABLE 32-continued

| | Day | | | | | | | |
|---|---|---|---|---|---|---|---|---|
| | 0 | 1 | 2 | 3 | 4 | 5 | 6 | 7 |
| GEK 2.05 mM | 0.10 | | | 1.73 | 2.40 | 2.65 | 2.64 | 3.05 |
| DGP 1.11 mM | 0.10 | | | 1.15 | 2.52 | 2.58 | 3.50 | 3.01 |
| standard deviation | | | | | | | | |
| basal medium | 0.00 | | | 0.15 | 0.33 | 0.48 | 0.81 | 0.33 |
| medium supplemented with vitamins and the like | 0.00 | | | 0.06 | 0.00 | 0.18 | 0.16 | 0.39 |
| GEK 2.05 mM | 0.00 | | | 0.36 | 0.41 | 0.29 | 0.27 | 0.10 |
| DGP 1.11 mM | 0.00 | | | 0.16 | 0.14 | 0.21 | 1.07 | 0.07 |

TABLE 33

| | Day | | | | | | | |
|---|---|---|---|---|---|---|---|---|
| | 0 | 1 | 2 | 3 | 4 | 5 | 6 | 7 |
| Viability (%) | | | | | | | | |
| basal medium | 98.0 | | | 94.00 | 88.33 | 83.67 | 74.67 | 68.33 |
| medium supplemented with vitamins and the like | 98.0 | | | 97.00 | 95.00 | 93.50 | 91.50 | 86.50 |
| GEK 2.05 mM | 98.0 | | | 97.00 | 97.00 | 95.33 | 84.33 | 79.00 |
| DGP 1.11 mM | 98.0 | | | 97.50 | 97.50 | 94.50 | 87.00 | 81.50 |
| standard deviation | | | | | | | | |
| basal medium | 0.0 | | | 3.00 | 8.08 | 9.02 | 12.58 | 9.29 |
| medium supplemented with vitamins and the like | 0.0 | | | 0.00 | 2.83 | 2.12 | 4.95 | 0.71 |
| GEK 2.05 mM | 0.0 | | | 1.00 | 1.00 | 3.79 | 12.66 | 8.19 |
| DGP 1.11 mM | 0.0 | | | 0.71 | 2.12 | 0.71 | 0.00 | 0.71 |

From Table 32, FIG. 30, Table 33, and FIG. 31, it was found that the addition of peptides to the basal medium or the medium supplemented with vitamins and the like increased both the viable cell count and the viability under the above-mentioned testing conditions.

After the third day of culture, 150 μL out of 200 μL of the culture medium recovered from each well of the 24-well (Deep well) cassette was subjected to a centrifugation operation (5,000 rpm, for 5 minutes) in a 1.5 mL tube, and the supernatant was separately recovered to measure the amount of produced protein by ELISA.

Figure 32:
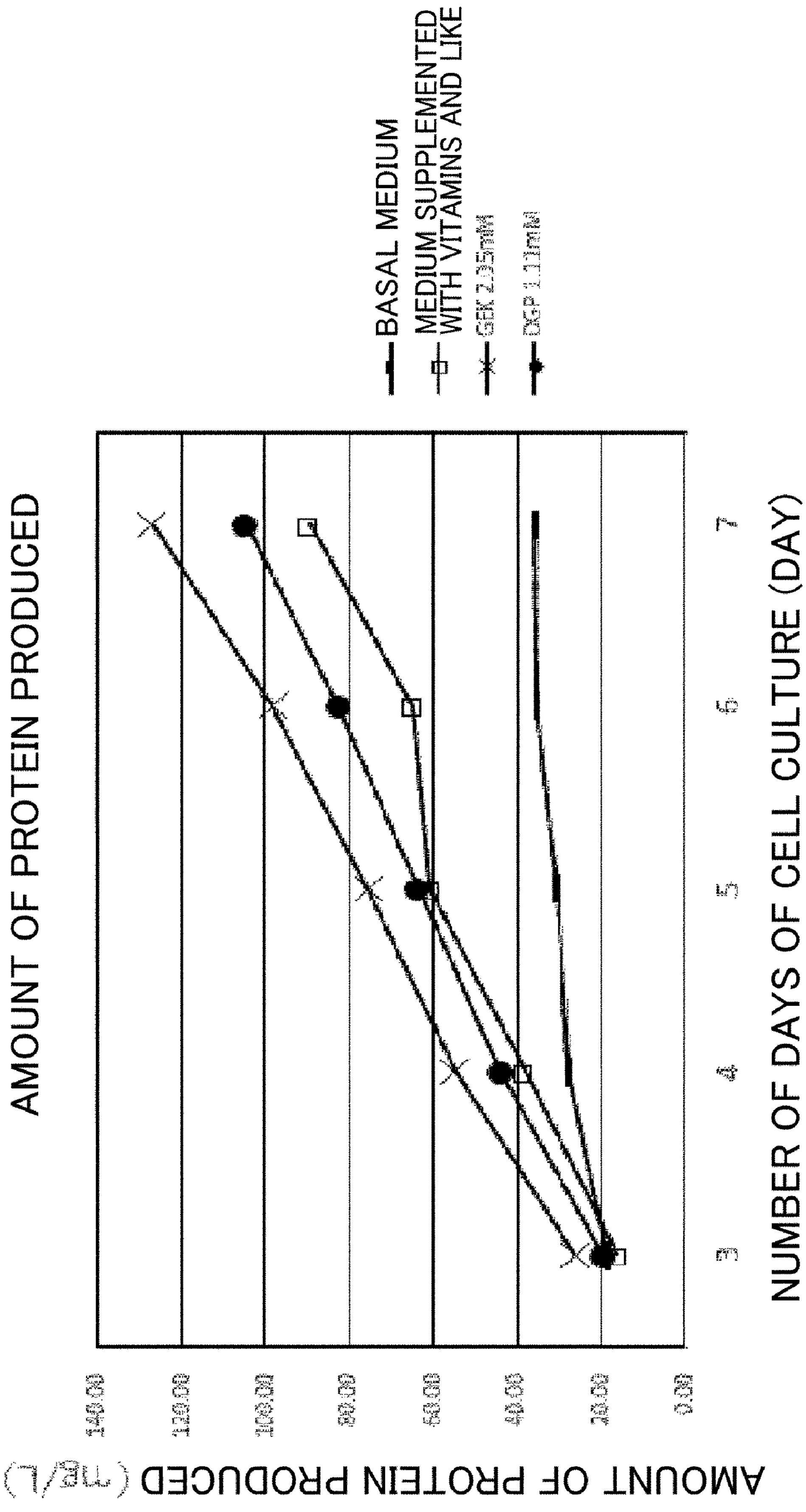

Table 34 and FIG. 32 show the measured amount of protein produced.

TABLE 34

| Amount of protein produced (mg/L) | Day | | | | |
|---|---|---|---|---|---|
| | 3 | 4 | 5 | 6 | 7 |
| Basal medium | 18.64 | 27.76 | 30.61 | 35.40 | 35.89 |
| Medium supplemented with vitamins and the like | 16.34 | 38.33 | 60.83 | 64.83 | 89.44 |
| GEK 2.05 mM | 26.32 | 54.96 | 75.54 | 98.46 | 127.08 |
| DGP 1.11 mM | 19.86 | 43.99 | 63.65 | 82.54 | 104.75 |

TABLE 34-continued

| | Day | | | | |
|---|---|---|---|---|---|
| Standard deviation | 3 | 4 | 5 | 6 | 7 |
| Basal medium | 4.59 | 5.86 | 8.45 | 8.86 | 12.55 |
| Medium supplemented with vitamins and the like | 1.14 | 2.61 | 5.64 | 9.90 | 15.29 |
| GEK 2.05 mM | 6.02 | 8.53 | 11.17 | 7.64 | 5.38 |
| DGP 1.11 mM | 5.64 | 10.12 | 10.01 | 5.74 | 7.60 |

From Table 34 and FIG. 32, it was found that the addition of peptides to the basal medium or the medium enriched with vitamins and the like increased the amount of protein produced.

(Protein Production Test on AGK and GPP in Floating Cell System)

Peptides having the sequences of Ala-Gly-Lys (AGK) and Gly-Pro-Pro (GPP) were synthesized to prepare peptide solutions of 5.53 mM of Ala-Gly-Lys (AGK) and 6.16 mM of Gly-Pro-Pro (GPP).

5 mL of each of a basal medium, a medium supplemented with vitamins and the like (basal medium+a component supplemented with vitamins and the like), and each peptide solution was added to each well of a 24-well (Deep well) cassette of Micro-24 Bioreactor System (manufactured by Nihon Pall Corporation) to perform culture overnight under the conditions of 37° C., pH 7, and 650 rpm. On the next day, pH calibration was performed, and thereafter 2 mL of the cell suspension prepared at $3.5\times10^5$ cells/mL was added to each well of the 24-well (Deep well) cassette, seeded such that the cell density of the floating cells was $1\times10^5$ cells/mL (7 mL/well), and cultured in the following evaluation medium under culture conditions of 37° C., pH 7, 650 rpm, and dissolved oxygen of 30%.

<Evaluation Medium>

Basal medium

Medium supplemented with vitamins and the like (basal medium+component supplemented with vitamins and the like)

AGK (3.95 mM)+medium supplemented with vitamins and the like

GPP (4.40 mM)+medium supplemented with vitamins and the like

As a culture medium, a basal medium in which 200 nM of methotrexate, 10 μg/mL of insulin, 5.5 μg/mL of transferrin, 6.7 ng/mL of sodium selenite, 10 μL/mL of Anti-Clumping Agent, and 10 μL/mL of 10% Pluronic F68 were blended in a DMEM/F12 culture medium (Gibco) was used.

As the floating cells used, serum-free floating CHO DP-12 obtained by acclimating CHO DP-12 (ATCC, Cat. No. CRL-12445) to serum-free flotation and subculturing using a 100 mL volume Erlenmeyer flask and with a shaking culture device (Custom Bio Shaker CO2-BR-43FL, TAITEC CORPORATION) under the culture conditions of 37° C., 5% $CO_2$, and a stirring speed of 125 rpm was used.

Table 31 shows the above-mentioned component supplemented with vitamins and the like.

After the third day of culture, 150 μL of the culture medium was recovered in a 1.5 mL tube from each well of the 24-well (Deep well) cassette to perform a centrifugation operation (5,000 rpm, for 5 minutes), and the supernatant was recovered to measure the amount of produced protein by ELISA.

Figure 33:
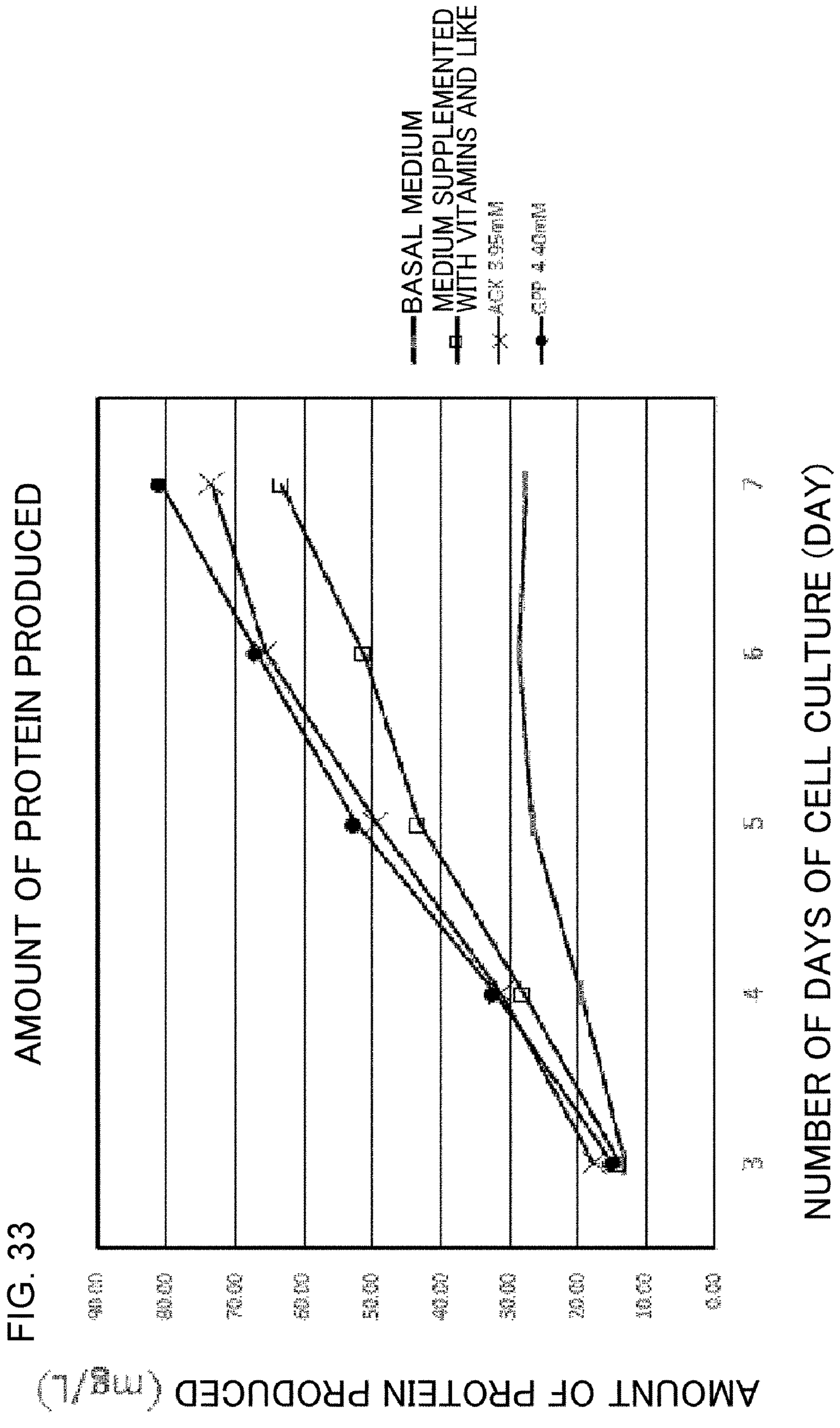

Table 35 and FIG. 33 show the measured amount of protein produced.

TABLE 35

| Amount of protein produced (mg/L) | Day 3 | 4 | 5 | 6 | 7 |
|---|---|---|---|---|---|
| Basal medium | 13.11 | 19.59 | 26.73 | 28.57 | 27.65 |
| Medium supplemented with vitamins and the like | 13.96 | 28.00 | 43.26 | 51.30 | 63.31 |
| AGK 3.95 mM | 17.74 | 31.36 | 49.43 | 65.58 | 73.46 |
| GPP 4.40 mM | 14.95 | 32.30 | 52.53 | 67.01 | 80.86 |
| **Standard deviation** | **Day 3** | **4** | **5** | **6** | **7** |
| Basal medium | 2.60 | 6.39 | 7.17 | 11.01 | 10.42 |
| Medium supplemented with vitamins and the like | 1.93 | 6.75 | 11.09 | 16.74 | 15.34 |
| AGK 3.95 mM | 1.73 | 0.99 | 2.67 | 5.86 | 6.88 |
| GPP 4.40 mM | 0.94 | 1.34 | 5.68 | 13.16 | 11.46 |

From Table 35 and FIG. 33, it was found that the addition of peptides to the basal medium or the medium supplemented with vitamins and the like increased the amount of protein produced under the above-mentioned testing conditions.

In addition, in the protein production in the above-mentioned floating cell system, the CHO cells were serum-free floating, but may be acclimated by first, performing cell culture using only a serum culture medium, thereafter performing cell culture in half a serum culture medium and a serum-free culture medium, and finally performing cell culture using only a serum-free culture medium.

Furthermore, in the protein production test in the above-mentioned floating cell system, the CHO cells were used, but the culture medium containing the peptide of the present invention is also applicable to cell lines such as hybridomas, HEK293, COS, and Sf9 which are utilized to produce other substances.

The protein production method using the peptide of the present invention may include a step of fed-batch culture in which a culture medium is replenished during production, in addition to the above-mentioned batch culture.

The invention claimed is:

1. A cell growth method, comprising:

acclimating animal cells to serum-free flotation using a basal medium, adding one of peptides selected from the group consisting of Gly-Glu-Lys (GEK), Asp-Gly-Pro (DGP), Ala-Gly-Lys (AGK), Gly-Pro-Pro (GPP), Gly-Gly-Pro (GGP), Ala-Glu-Lys (AEK), Ala-Gly-Gly (AGG), Ala-Ser-Asn (ASN), and Glu-Gly-Lys (EGK), to the basal medium, and seeding the animal cells acclimated to the basal medium in the basal medium to which the peptides have been added to perform cell growth.

* * * * *